US009168011B2

(12) United States Patent
Nenoki et al.

(10) Patent No.: US 9,168,011 B2
(45) Date of Patent: Oct. 27, 2015

(54) RADIOGRAPHY SYSTEM, CONSOLE AND ELECTRONIC CASSETTE

(75) Inventors: Yasuyo Nenoki, Ashigarakami-gun (JP); Haruka Ikegame, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 665 days.

(21) Appl. No.: 13/340,931

(22) Filed: Dec. 30, 2011

(65) Prior Publication Data

US 2012/0195407 A1 Aug. 2, 2012

(30) Foreign Application Priority Data

Jan. 27, 2011 (JP) .................................. 2011-015503

(51) Int. Cl.
*G03B 42/04* (2006.01)
*A61B 6/00* (2006.01)

(52) U.S. Cl.
CPC ............ *A61B 6/4283* (2013.01); *A61B 6/4405* (2013.01); *A61B 6/4494* (2013.01); *A61B 6/461* (2013.01); *A61B 6/463* (2013.01); *A61B 6/468* (2013.01); *A61B 6/545* (2013.01);
(Continued)

(58) Field of Classification Search
CPC ...... A61B 6/44; A61B 6/4283; A61B 6/4405; A61B 6/4494; A61B 6/461; A61B 6/463; A61B 6/545; A61B 6/587; A61B 6/4266; G03B 42/04; G03B 42/047
USPC ............. 378/19, 91, 98, 98.5, 98.8, 162, 165, 378/167, 169, 172, 189, 204, 210; 250/370.01, 370.08, 370.09, 271, 371, 250/491.1, 526
See application file for complete search history.

(56) References Cited

U.S. PATENT DOCUMENTS

| 4,739,480 | A  | * | 4/1988 | Oono et al. ................... 250/584 |
| 6,044,131 | A  | * | 3/2000 | McEvoy et al. ............... 378/162 |
| 2003/0142119 | A1 | * | 7/2003 | Akagi ........................... 345/698 |

(Continued)

FOREIGN PATENT DOCUMENTS

| JP | 2010187734 A | 9/2010 |
| JP | 2010-268822 A | 12/2010 |
| JP | 2011235093 A | 11/2011 |

OTHER PUBLICATIONS

Notification of Reasons for Refusal, dated Feb. 26, 2013, issued in corresponding JP Application No. 2011-015503, 6 pages in English and Japanese.

(Continued)

*Primary Examiner* — Anastasia Midkiff
(74) *Attorney, Agent, or Firm* — Sughrue Mion, PLLC

(57) ABSTRACT

For identification of individual electronic cassettes, a different label is attached to each of the electronic cassettes. Selection buttons for selecting one of the electronic cassettes are provided on a console in correspondence with the respective electronic cassettes. A cassette ID is assigned to each of the electronic cassettes, and the console communicates with the selected electronic cassette using the cassette ID assigned to the selected electronic cassette. Data of correspondence between the cassette ID and the label is memorized for each electronic cassette. The same label is displayed on the selection button as the label on the corresponding electronic cassette, allowing confirming whether the electronic cassette actually positioned for imaging coincides with the electronic cassette selected on the console.

19 Claims, 18 Drawing Sheets

(52) U.S. Cl.
CPC .............. *A61B 6/587* (2013.01); *G03B 42/047* (2013.01); *A61B 6/4266* (2013.01); *G03B 42/04* (2013.01)

(56) References Cited

U.S. PATENT DOCUMENTS

| | | | | |
|---|---|---|---|---|
| 2004/0089826 A1* | 5/2004 | Yonekawa | ..................... | 250/584 |
| 2004/0094732 A1* | 5/2004 | Yonekawa | ..................... | 250/589 |
| 2005/0167623 A1* | 8/2005 | Yonekawa | ..................... | 250/589 |
| 2005/0227154 A1* | 10/2005 | Motoki | ..................... | 430/22 |
| 2006/0054839 A1* | 3/2006 | Yonekawa | ..................... | 250/484.4 |
| 2008/0317214 A1* | 12/2008 | Maack | ..................... | 378/162 |
| 2011/0069814 A1* | 3/2011 | Yonekawa | ..................... | 378/62 |

OTHER PUBLICATIONS

Notification of Reasons for Refusal, drafted Sep. 30, 2014, issued in corresponding JP Application No. 2011-015503, 2 pages in English.

* cited by examiner

FIG.6

| ACQUISITION ORDER 1 | FRONTAL IMAGING OF CHEST IN UPRIGHT POSITION (A-P) |
| --- | --- |
| ACQUISITION ORDER 2 | FRONTAL IMAGING OF ABDOMEN IN UPRIGHT POSITION (P-A) |
| ACQUISITION ORDER 3 | FRONTAL IMAGING OF ABDOMEN IN RECUMBENT POSITION (A-P) |

| EXAMINATION ORDER (PATIENT ID:001) |
| --- |
| EXAMINATION ORDER (PATIENT ID:002) |
| EXAMINATION ORDER (PATIENT ID:003) |
| EXAMINATION ORDER (PATIENT ID:004) |
| EXAMINATION ORDER (PATIENT ID:005) |

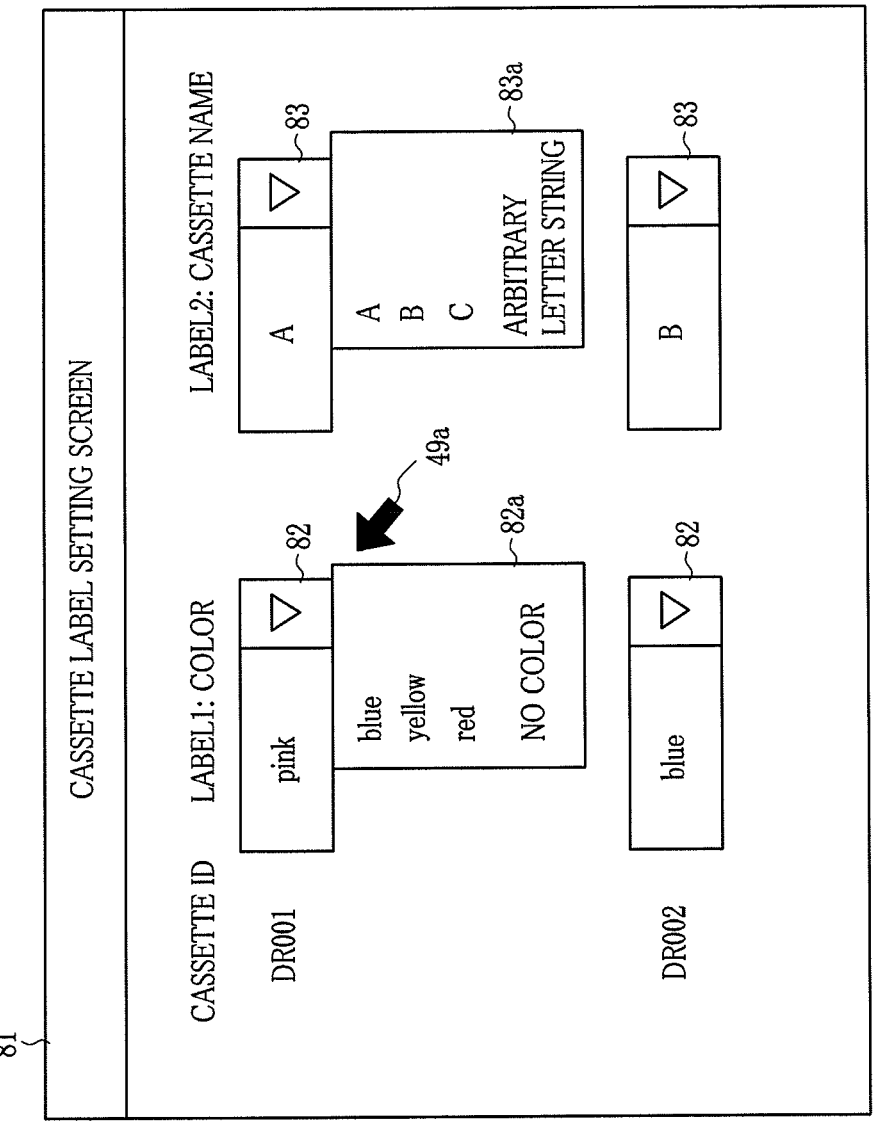

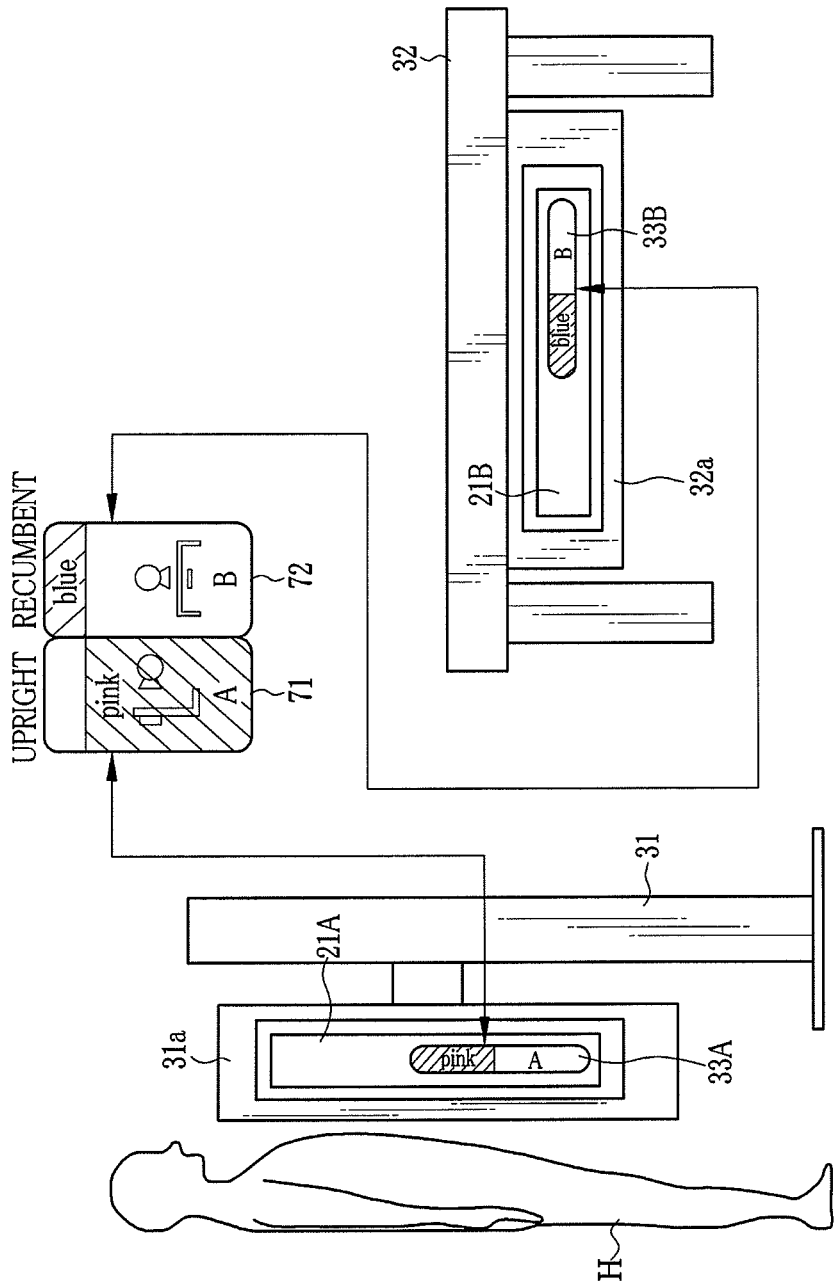

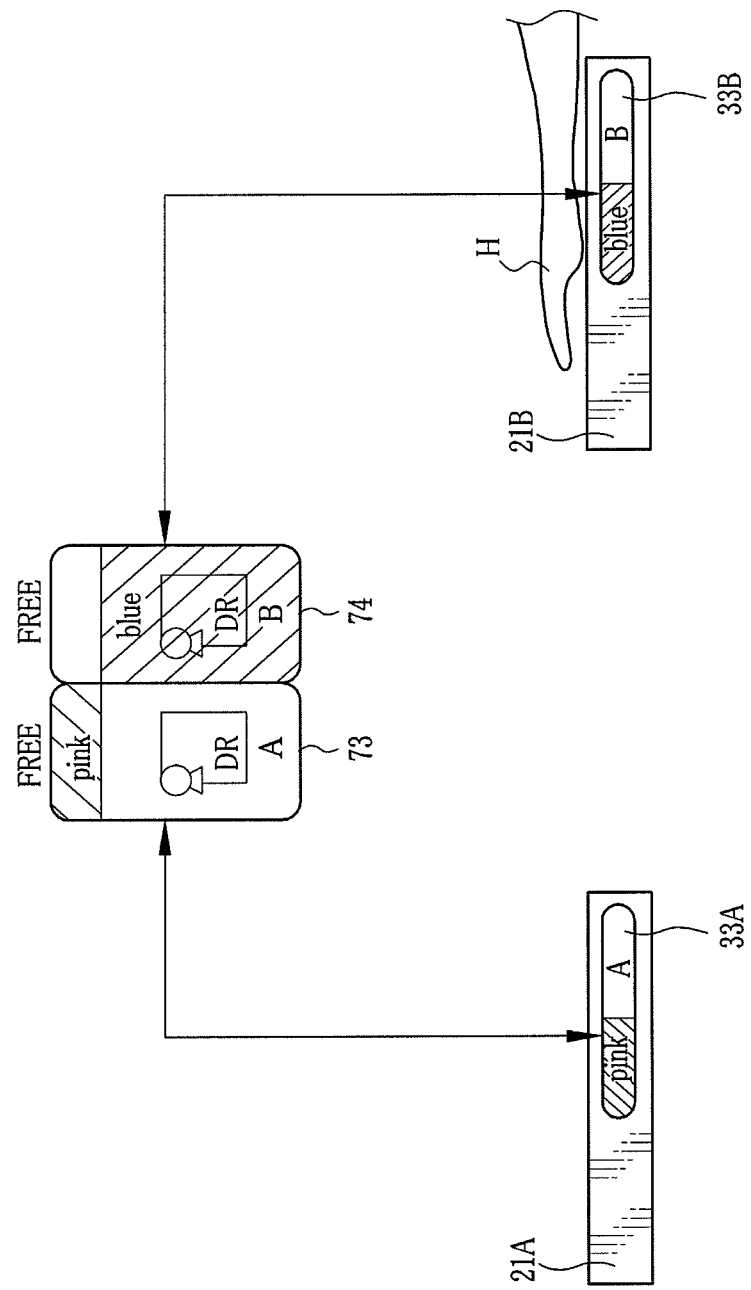

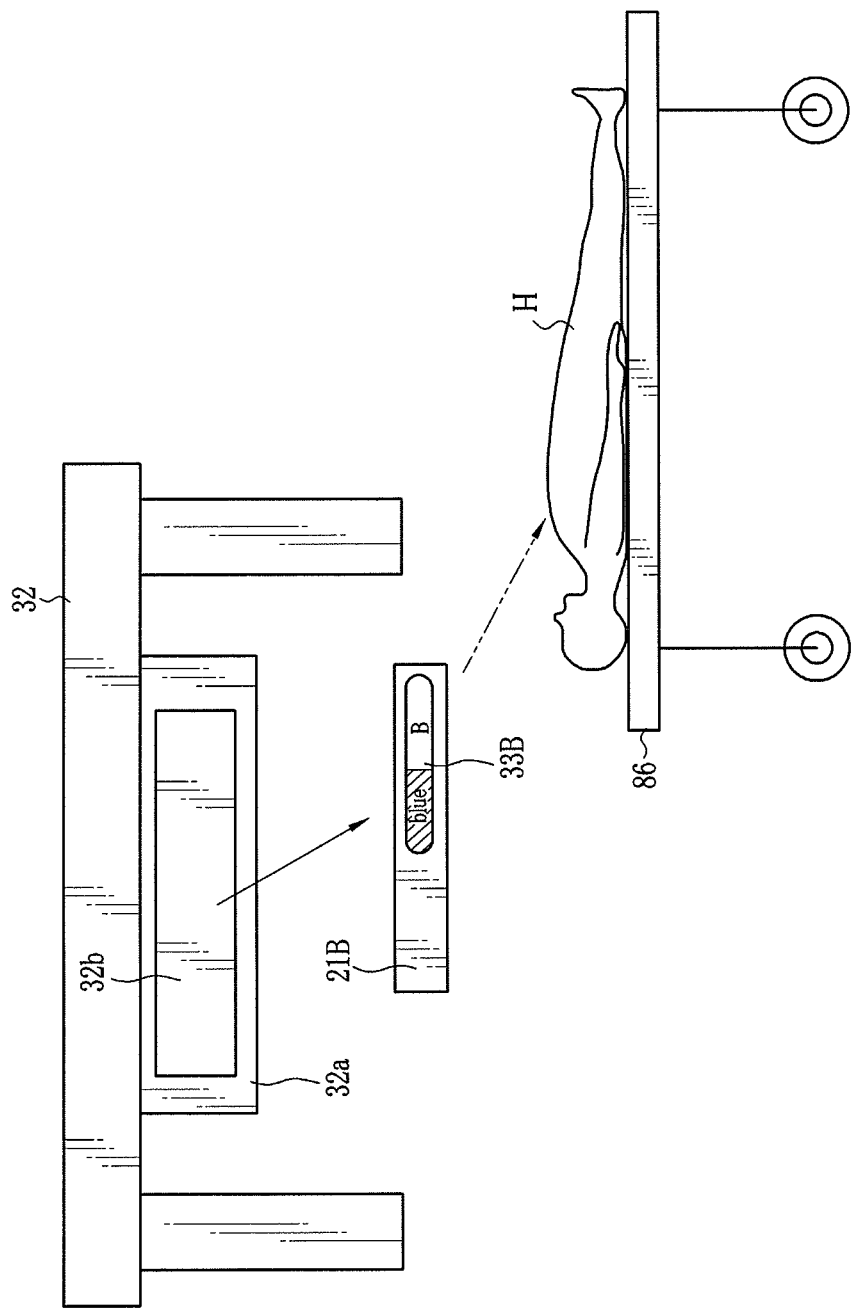

RADIOGRAPHY SYSTEM, CONSOLE AND ELECTRONIC CASSETTE

BACKGROUND OF THE INVENTION

1. Field of the Invention

The present invention relates to a radiography system using electronic cassettes to take radiographs, a console and the electronic cassettes for the radiography system.

2. Description of the Related Art

In the medical field, radiography systems utilizing radioactive rays, such as x-rays, for imaging are widely known. An x-ray radiography system includes an x-ray radiator having an x-ray source for radiating x-rays, and radiographic equipment for receiving x-rays as being projected from the x-ray radiator toward a subject and penetrating through the subject, thereby to acquire a radiograph or x-ray image representing information on the subject. As the radiographic equipment, an x-ray image detector using a flat panel detector (FPD) in place of conventional x-ray film or an imaging plate (IP) has recently been known, which can output digital data of an acquired x-ray image, as disclosed in JPA 2010-268822.

This prior art describes a built-in type x-ray image detector that is integrated in a radiographic stand for imaging in the upright position or a radiographic table for imaging in the recumbent position, and an electronic cassette for radiography, a portable x-ray image detector containing a FDP in a portable housing. The electronic cassette for radiography, hereinafter called simply as the electronic cassette, may be used in a position on a bed on which a patient lies, or a position held by a patient in order to acquire images from such part of the patient, e.g. leg or arm, that is hard to capture by the built-in type image detector. Either type of the x-ray image detectors is controllable on a console.

As described in the prior art, a radiologist in charge of radiography selects a suitable type of x-ray image detector from among a variety of x-ray image detectors according to an examination order that is received from a requester for the radiography. The patient or subject of the examination is led to the x-ray image detector, and the x-ray image detector is positioned to the target site of the subject. Acquisition settings and other control data are transmitted from the console to the selected x-ray image detector. When an image is acquired by the selected x-ray image detector from the subject irradiated with the x-ray, the console receives image data of the acquired image from the selected x-ray image detector and displays the acquired image on a screen.

As disclosed in FIG. 4 and paragraph 0038 of JPA 2010-268822, the console is configured to display an operating screen that is provided with a number of selection buttons corresponding to a previously registered various kinds of x-ray image detectors. The selection buttons on the operating screen have icons that schematically show respective appearances of the corresponding x-ray image detectors, to facilitate selecting an appropriate one of these x-ray image detectors.

Displaying an icon of the corresponding image detector on each selection button, like in the above prior art, enables the radiologist to compare the icons with the appearances of the actual x-ray image detectors and confirm that the x-ray image detector selected on the console coincides with the x-ray image detector to which the patient is positioned. If these image detectors do not coincide, no image will be acquired even while the patient is irradiated with x-rays. For the sake of operability and safety of the radiography system, it is very important making it easier for the radiologist to check whether the x-ray image detector selected on the console coincides with the x-ray image detector to which the patient is positioned.

Such icons that indicate appearances of different kinds of image detectors, as disclosed in the prior art, are useful for discriminating between those x-ray image detectors which differ apparently from each other, e.g. a stationary image detector like the radiographic stand or table and a portable electronic cassette. However, it is difficult for the icons to clearly show the difference between those image detectors which have similar or identical appearances, like the electronic cassettes. In that case, it becomes difficult to confirm the coincidence between the image detector selected on the console and the image detector actually positioned to the subject.

According to a survey of x-ray image detectors used in medical facilities, a radiographic stand and a radiographic table are installed in one x-ray room in many cases, and in few cases two or more stationary x-ray image detectors of the same kind, like multiple radiographic stands or multiple radiographic tables, are installed. To the contrary, there are many medical facilities that use a plurality of electronic cassettes in one x-ray room.

Such electronic cassettes that have substantially the same size as the conventional film cassettes and IP cassettes, 14 by 17 inch, have recently been popular. This type electronic cassette may be used independently but also as a substitute for the stationary image detector. That is, the electronic cassette may be mounted in a conventional radiographic stand or table that has been used in combination with the film cassette or the IP cassette.

Although the capability of the electronic cassettes for use in many styles or modes is convenient, frequent attaching or detaching operation of the electronic cassette to or from the radiographic stand or table may cause confusion with other electronic cassettes because they have identical or similar appearance. The probability of confusing and misplacing the electronic cassettes will increase as the number of available electronic cassettes increases. Especially in a hospital where two or more radiologists deal with the electronic cassettes, the confusion and misplacement of the electronic cassettes will be more likely to happen. Therefore, a solution has been desired that makes it easier and surer for the radiologist to confirm whether the electronic cassette positioned to the subject of examination is equal to the one selected on the console. The above mentioned prior art does not disclose nor imply this problem and any solution therefor.

SUMMARY OF THE INVENTION

In view of the foregoing, an object of the present invention is to provide a solution for making it easier and surer to confirm whether the electronic cassette positioned to the subject of radiography coincides with the one selected on the console.

To achieve the above object, the present invention provides a radiography system using an electronic cassette having an image detector and a portable housing containing the image detector. The radiography system of the present invention comprises a label attached to the housing of the electronic cassette, for making the electronic cassette visually distinguishable from other electronic cassettes; a console that communicates with a selected one of plurality of the electronic cassettes; a first storage device storing first correspondence data that indicates correspondence between the label and a cassette ID given to each of the electronic cassettes, the cassette ID being used by the console for communication with the selected electronic cassette; and a control device provided in the console, the control device referring to the first correspondence data to display the label that corresponds to the cassette ID of the selected electronic cassette on a screen.

Preferably, the label includes at least one of colors, letters, numerals, symbols and patterns as an element.

More preferably, the label includes a color as an element.

The housing is preferably provided with at least a labeling portion on which the label is sealed.

The control device may preferably display an operating screen using a graphical user interface. The operating screen has a plurality of selection buttons for respective selection of the electronic cassettes. Each of the selection buttons is assigned to the cassette ID of one of the electronic cassettes, and the label corresponding to the assigned cassette ID is displayed on each selection button.

Preferably, the label is continuously displayed on each of the selection buttons regardless of whether selected or not. In this embodiment, the control device changes the condition of the label displayed on a selected one of the selection buttons to make the selected selection button distinguishable from others.

In an embodiment, each label may include a color as an element, and each of the selection buttons is displayed in first and second colors, the first color being common to all of the selection buttons, the second color being different from one cassette ID to another corresponding to the color of the label. In this embodiment, the first color and the second color are replaced with each other on the selected selection button.

The electronic cassettes are usable in different modes of usage, including a mode of usage mounted in a radiographic stand or table, and a mode of usage free from the radiographic stand or table. It is therefore preferable to provide two or more selection buttons for one cassette ID such that each of the selection buttons is assigned to one mode of usage.

Preferably, the modes of usage assigned to the selection buttons include a mode of usage in which said electronic cassette is mounted in a radiographic stand for imaging in upright position, and a mode of usage in which the electronic cassette is mounted in a radiographic table for imaging in decumbent position.

The console is preferably provided with an acquisition order receiving device for receiving acquisition orders including data of designating the mode of usage of the electronic cassette.

Preferably, the radiography system further includes a second storage device for storing second correspondence data indicating correspondence between the modes of usage and the selection buttons, wherein the control device determines one of the selection buttons on the basis of the acquisition order and the second correspondence data, and sets the determined selection button to the selected state to select automatically one electronic cassette to be used for imaging from among the electronic cassettes.

The first correspondence data is preferably modifiable.

The console preferably includes a modification accepting device that may access the first storage device to modify the first correspondence data in response to modifying operations.

In an embodiment, the cassette ID may be stored in a memory built in the electronic cassette.

The first storage device may be an internal storage device incorporated in the console, or an external storage device connectable to the console through a network.

The first storage device may also be a memory built in the electronic cassette.

The electronic cassette may preferably be of a wireless type that wirelessly communicates with the console.

The housing of the electronic cassette may preferably be of a size according to ISO 4090:2001.

The present invention also provides a console that communicates with an electronic cassette selected from among a plurality of electronic cassettes for radiography. The console of the present invention comprises a correspondence data reading device for reading first correspondence data from a storage device, the first correspondence data indicating correspondence between a cassette ID of the electronic cassette and a label attached to a housing of the electronic cassette for making the electronic cassette visually distinguishable from other electronic cassettes, the cassette ID being used by the console for communication with the selected electronic cassette; and a control device for displaying the label that corresponds to the cassette ID of the selected electronic cassette on a screen with reference to the first correspondence data.

An electronic cassette according to the present invention comprises an image detector for detecting radiographic images when irradiated with radioactive rays; a portable housing containing the image detector; a labeling portion provided on the housing of the electronic cassette, a label for making the electronic cassette visually distinguishable from other electronic cassettes being attached to the labeling portion; a communication device for communication with a console; and a memory storing a cassette ID that is used for communication with the console and the label assigned to the cassette ID.

According to the present invention, the label corresponding to the label on the selected electronic cassette is displayed on the console. Therefore, it becomes easier and surer for the operator or radiologist to confirm whether the electronic cassette selected on the console coincides with the one positioned to the subject of radiography.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 6 is an explanatory diagram illustrating an order for examination;

FIG. 11 is an explanatory diagram illustrating a cassette label setting screen;

FIG. 12 is an explanatory diagram illustrating a condition of the selection buttons where upright position imaging is selected;

FIG. 13 is an explanatory diagram illustrating a condition of the selection buttons where one of two electronic cassettes is selected;

FIG. 14 is an explanatory diagram illustrating a position of the electronic cassette removed from a radiographic table for use independently;

DESCRIPTION OF THE PREFERRED EMBODIMENTS

Figure 1:
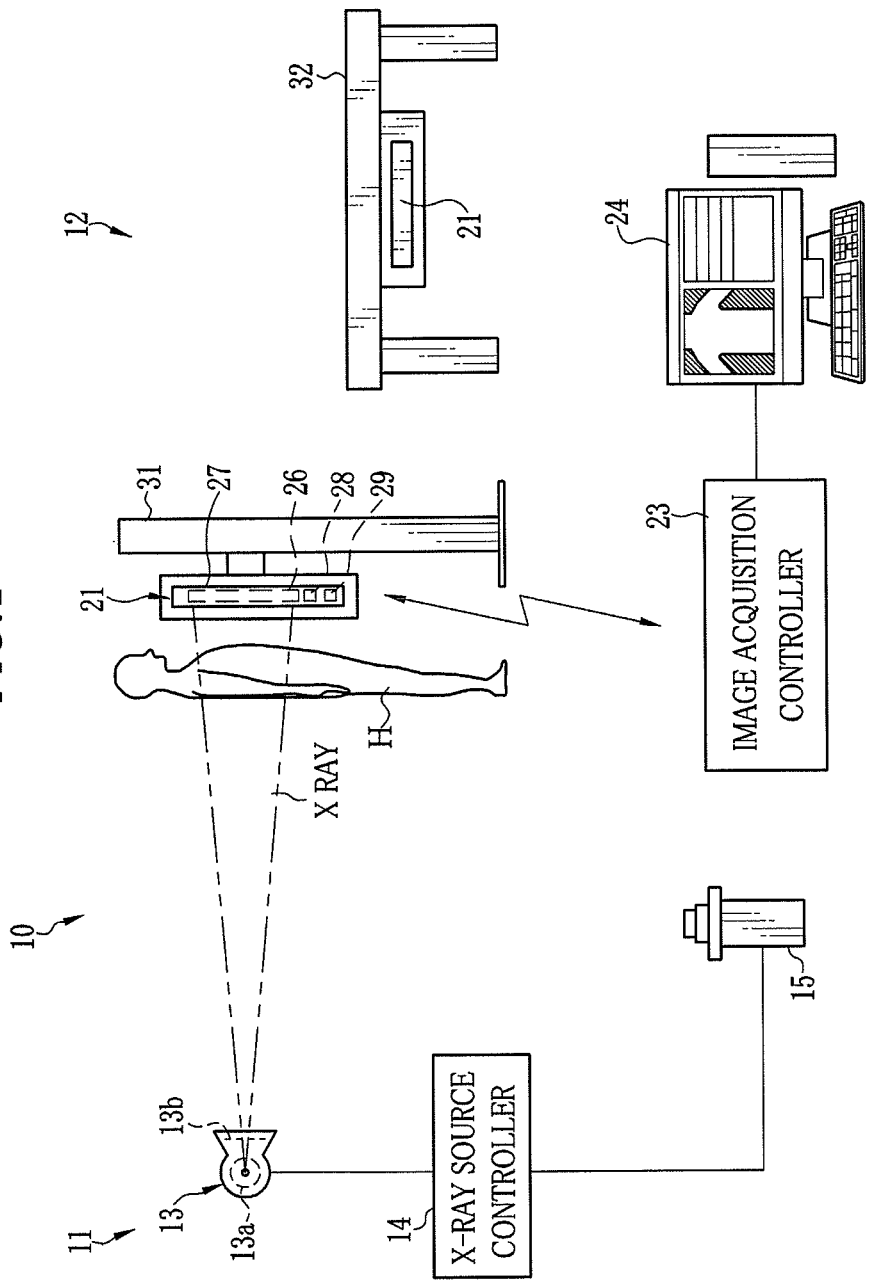
FIG. 1 is a diagram schematically illustrating a radiography system.

In FIG. 1, a radiography system 10 consists of an x-ray radiator 11 and radiographic equipment 12. The x-ray radiator 11 consists of an x-ray source 13, an x-ray source controller 14 for controlling the x-ray source 13, and an activator switch 15. The x-ray source 13 has an x-ray tube 13a for radiating x-rays and a collimator 13b for limiting the irradiation field of x-rays from the x-ray tube 13a.

The x-ray tube 13a has a cathode which includes a filament for emitting thermions and an anode (target) against which the thermions strike to radiate x-rays. The collimator 13b may for example be made of lead plates shielding x-rays, which are put together in a double-cross formation to form a center aperture for letting x-rays pass through it. The lead plates are movable to change the size of the center aperture so as to confine the radiation field to a suitable range.

The x-ray source controller 14 includes a high voltage generator for supplying a high voltage to the x-ray source 13, and a controller for controlling tube voltage, tube current and x-ray radiation time, wherein the tube voltage determines energy spectra of x-rays from the x-ray source 13, and the tube current determines the amount of radiation per unit time. The high voltage generator generates the high tube voltage by boosting an input voltage through a transducer, and supplies the tube voltage as the driving power to the x-ray source 13 through a high voltage cable. The tube voltage, the tube current and the x-ray radiation time are acquisition settings for the radiographic equipment 12, which may be manually set by a radiologist or operator using an operation panel of the x-ray source controller 14. In addition, acquisition settings may be decided by instructions from the radiographic equipment 12 through a communication cable.

The activator switch 15 is operated by the radiologist, and is connected to the x-ray source controller 14 through a signal cable. The activator switch 15 may be a two-step push button switch that outputs a warm-up start signal for staring warming up the x-ray source 13 upon being pushed to the first step, and then outputs a radiation start signal upon being pushed further to the second step, letting the x-ray source 13 start radiations. These signals are fed through the signal cable to the x-ray source controller 14.

The x-ray source controller 14 controls the operation of the x-ray source 13 according to the control signals from the activator switch 15. Upon receipt of the radiation start signal from the activator switch 15, the x-ray source controller 14 starts supplying the power to the x-ray source 13 and also activates a timer to start counting the x-ray radiation time. The x-ray source controller 14 stops the x-ray source 13 from radiation when the radiation time, one of the image acquiring conditions, is over. The x-ray radiation time is variable depending upon other image acquiring conditions, but the maximum x-ray radiation time for acquisition of a still image is mostly set in the range of about 500 ms to about 2 sec. Therefore, the radiation time is limited at most to the maximum radiation time.

The radiographic equipment 12 consists of an electronic cassette 21 for radiography, an image acquisition controller 23 and a console 24. The electronic cassette 21 mainly consists of a flat panel detector (FPD) 26 as a radiographic image detector and a housing 27 containing the FPD 26. The electronic cassette 21 is a portable x-ray image detector that receives x-rays from the x-ray source 13 after penetrating through a test subject or patient H, to detect an x-ray image or radiograph of the test subject H.

The electronic cassette 21 is provided with a communicator 29 for communication with the console 24 and a memory 28 storing a cassette ID. The cassette ID is information necessary for the console 24 to identify each individual cassette 21 among many cassettes 21 communicably connected to the console 24. The cassette ID is attached to communication data that is exchanged between the console 24 and each cassette 21.

Figure 2:
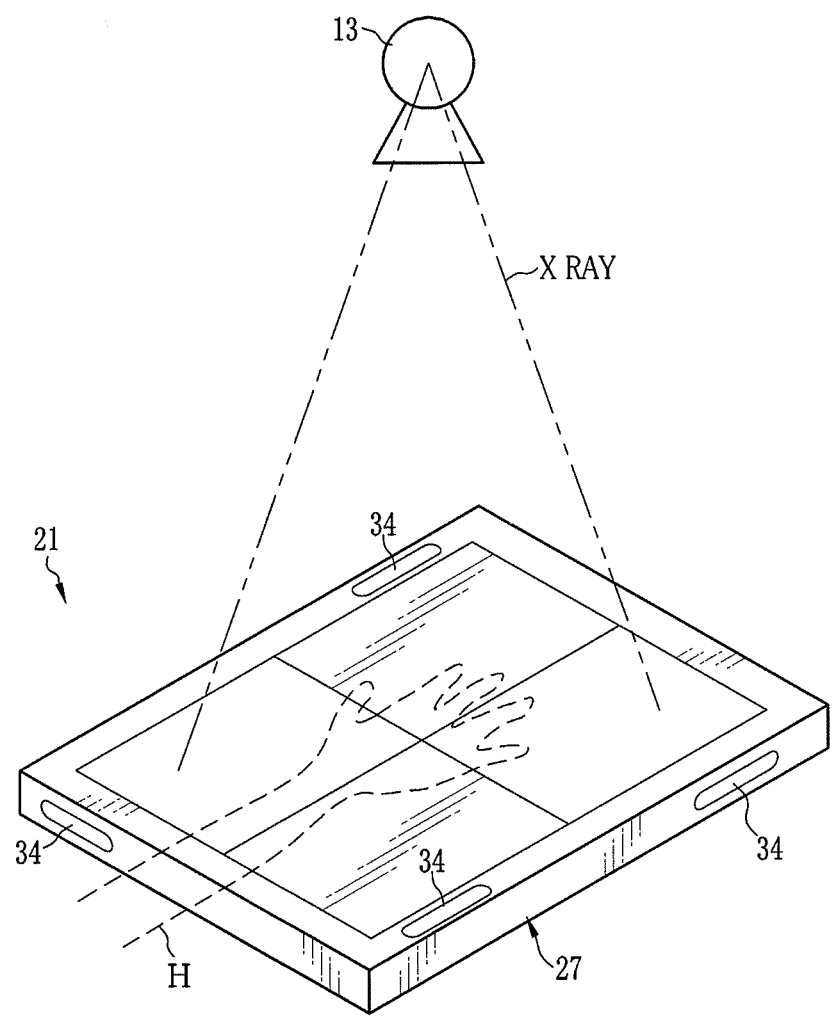
FIG. 2 is explanatory diagram illustrating an electronic cassette in a free position of usage.

The housing 27 of the electronic cassette 21 has a flat planer body having substantially rectangular top and bottom surfaces (see FIG. 2). The plane size of the electronic cassette 21 is about the same as that of radiographic film cassettes and IP cassettes (imaging plate cassettes) which may be called computed radiography cassettes (CR cassette), i.e. 14 by 17 inch, dimensioned according to ISO 4090:2001 standard.

In operation, the electronic cassette 21 can be detachably attached to a radiographic stand 31 for imaging the subject H in the upright position or a radiographic table 32 for imaging the subject H in the recumbent position. The radiographic stand 31 and the radiographic table 32 may be conventional ones that can also be used with other types of radiographic cassettes like film cassettes and IP cassettes. As having the same size as the film cassettes and IP cassettes, the electronic cassette 21 can be mounted to the conventional radiographic stand or table 31 or 32, and thus substituted for a floor type x-ray image detector having a flat panel detector (FPD) fixedly integrated therein.

Besides being used in the radiographic stand or table 31 or 32, the electronic cassette 21 may be used freely, as is shown in FIG. 2, for radiography of such parts of the subject H that can be hard or inconvenient to acquire images in the position mounted in the radiographic stand or table 31 or 32. Being usable separately from the radiographic stand or table 31 or 32 as well as in the radiographic stand or table 31 or 32, the electronic cassette 21 is convenient and easy to handle.

In general, a plurality of electronic cassettes 21, e.g. two cassettes 21, are disposed in an x-ray room such that one is mounted in a radiographic stand 31 and the other is mounted in a radiographic table 32, and when needed, any of these cassettes 21 is removed and used separately from the radiographic stand or table 31 or 32.

Unlike the film cassettes and the IP cassettes, the electronic cassette 21 has to communicate with the console 24 for actuation. Therefore, the operator must confirm that the electronic cassette 21 positioned to the subject H coincides with the one that is selected on the console 24 and communicating with the console 24.

It is impossible to distinguish the electronic cassettes 21 apparently from each other if they are the same model and have a completely identical appearance of the housing 27. Even between the electronic cassettes 21 of different models, they are difficult to distinguish because their housings 27 have similar appearances to each other as they are dimensioned similarly to the film cassettes and IP cassettes.

In order to make the electronic cassettes 21 distinguishable by naked eyes, a label 33 is put on the housing 27 of each cassette 21. The label 33 is made of an adhesive sheet having a label recording obverse surface and an adhesive reverse surface.

Figure 3A:
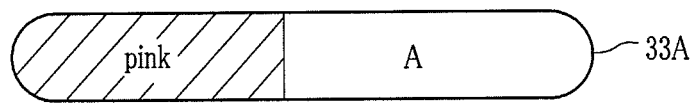
FIGS. 3A and 3B are explanatory diagrams illustrating labels for identifying individual electronic cassettes.
Figure 3B:
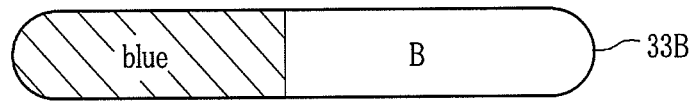

As shown for example in FIGS. 3A and 3B, the cassette label may consist of a color and a name given to each cassette within each unit of medical facilities like a hospital. Half of the recording surface of the label 33 is for the label color, as implied by hatching, and the other half is for indicating the cassette name.

One cassette 21 may be marked with a first label 33A that is colored pink in the half and recorded with a cassette name, and the other cassette 21 may be marked with a second label 33B that is colored blue in the half and recorded with a cassette name. The cassette names on the first and second labels 33A and 33B are represented by a letter "A" and a letter "B" respectively for brevity shake.

Note that the words "pink" and "blue" written in the hatched segments of the respective labels 33A and 33B are just indicating the color of each label for convenience in the white-and-black drawings. Namely, these words are not actually recorded on the labels.

These labels 33 on the housings 27 enable identification of the individual cassettes 21 even while they are not distinguishable by appearance. The elements of the label may be printed or hand-written on a sheet.

Figure 4:
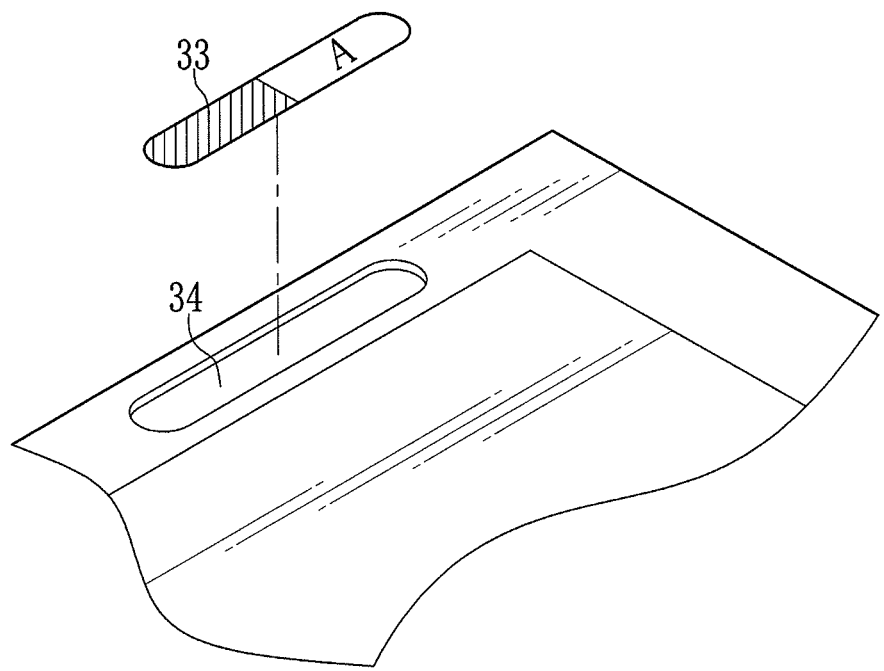
FIG. 4 is an explanatory diagram illustrating a labeling portion on an electronic cassette.

As shown in FIG. 4, the housing 27 is provided with at least a labeling portion 34 for putting the label 33 thereon. The labeling portion 34 is defined by a recess formed in a marginal portion of the outer surface of the housing 27, to have a corresponding size to the label 33. As shown for example in FIG. 2, the labeling portion 34 may be provided on each of the six sides of the housing 27. Providing these labeling portions 34 in predetermined portions of the housing 27 will standardize the positions of the labels 33 on the respective housings 27 of many cassettes 21, which will make the labels 33 more visible.

Figure 5A:
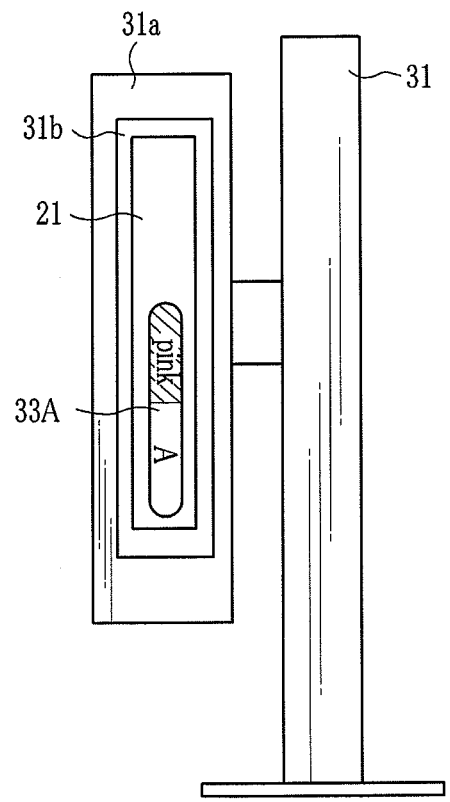
FIG. 5A is an explanatory diagram illustrating the electronic cassette mounted in a radiographic stand with one side of the cassette housing exposed.
Figure 5B:
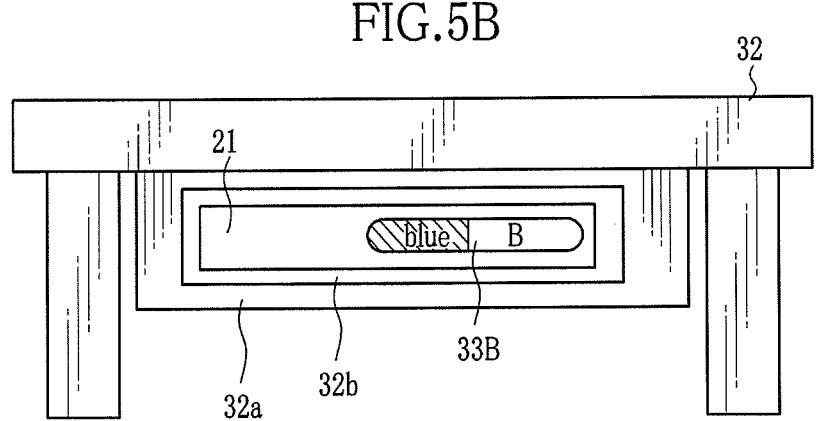
FIG. 5B is an explanatory diagram illustrating the electronic cassette mounted in a radiographic table with one side of the cassette housing exposed.

Moreover, as shown in FIGS. 5A and 5B, many of the radiographic stands 31 and the radiographic tables 32 have slot-type mounts 31a or 32b, into which the electronic cassette 21 is insertable through side slots 31b or 32b. In the position mounted in the slot-type mount 31a or 32a of the radiographic stand 31 or the radiographic table 32, one side of the electronic cassette 21 is exposed through the slot 31b or 32b. Therefore, the operator can identify the mounted cassette 21 from the label 33 that is put on the exposed side of the electronic cassette 21.

Referring back to FIG. 1, the electronic cassette 21 is of a wireless type, in which the communicator 29 includes a wireless communicator using radio waves or optical signals like infrared rays beside a wired communicator using a communication cable. The electronic cassette 21 may be powered through a power supply cable from a utility power source, or may also be powered by batteries. The wireless type cassette 21 is easy to deal with.

The image acquisition controller 23 is communicably connectable to the electronic cassette 21 through wired or wireless communication devices, so as to control the electronic cassette 21 according to instructions from the console 24. Specifically, the image acquisition controller 23 sends data of acquisition settings to the electronic cassette 21, to set up conditions for signal processing in the FPD 26, such as the gain at a voltage amplifier for signal charges accumulated in the FPD 26. The image acquisition controller 23 also receives a synchronizing signal from the x-ray radiator 11 and transfers the signal to the electronic cassette 21, thereby to synchronize the charge accumulation in the FPD 26 with the timing of radiation from the x-ray source 13.

In addition, the image acquisition controller 23 receives image data from the electronic cassette 21 and transfers the image data to the console 24. The image acquisition controller 23 also controls power supply to the electronic cassette 21 and switching between various modes, e.g. power-saving mode and imaging standby mode, according to the instructions from the console 24.

The console 24 is an operation terminal that communicates with the electronic cassette 21 via the image acquisition controller 23 and controls the electronic cassette 21 via the image acquisition controller 23. The console 24 is also provided with an examination order receiving function for receiving entries of orders for x-ray examinations issued by requesters, doctors in diagnosis and treatment departments, including internists and surgeons.

As shown in FIG. 6, the examination orders are issued for each patient. Each examination order includes information on the requestor (the doctor ID and the department), information on the patient (the name of patient and the patient ID), and acquisition orders. The examination order may include a single acquisition order or multiple acquisition orders. The acquisition order includes procedure information designating the target site of imaging, the imaging direction and the imaging position of the patient. The target site may include head, chest and abdomen. The imaging direction may include frontal, lateral and oblique. In the case of frontal imaging, whether it is posterior to anterior (P-A) irradiation or anterior to posterior (A-P) irradiation is designated. The P-A irradiation is projecting x-rays from the back of the patient or subject, whereas the A-P irradiation is projecting x-rays from the front. In the case of oblique imaging, whether x-rays should be projected in right oblique direction or in left oblique direction to the patient is designated.

In the example of FIG. 6, the examination order with patient ID "001" includes a first acquisition order requesting a procedure of frontal chest imaging in the upright position by the A-P irradiation, a second acquisition order requesting a frontal abdominal imaging in the upright position by the P-A irradiation, and a third acquisition order requesting a frontal abdominal imaging in the recumbent position by the A-P irradiation.

The examination orders may be issued by external systems, such as a hospital information system (HIS) and a radiological information system (RIS), which manage information on patients and information on x-ray examinations. The examination orders from the external systems may be fed to the console 24 through a communication network like a local area network (LAN). Alternatively, the operator or radiologist may manually input the examination orders in the console 24 with reference to handwritten orders. Before executing the imaging, the radiologist inputs conditions for image acquisition in the console 24 on the basis of the contents of the acquisition orders included in each examination order, so that the image acquisition controller 23 sets up the electronic cassette 21 according to the entered conditions for image acquisition.

Data of a radiograph acquired by the electronic cassette 21 is sent to the console 24 via the image acquisition controller 23. The console 24 processes the radiographic data so that a processed radiograph is displayed on a screen of the console 24. The processed radiographic image is also stored in a data storage device, such as a hard disc in the console 24 or an image database server that is communicably connected to the console 24 through a network.

Figure 7:
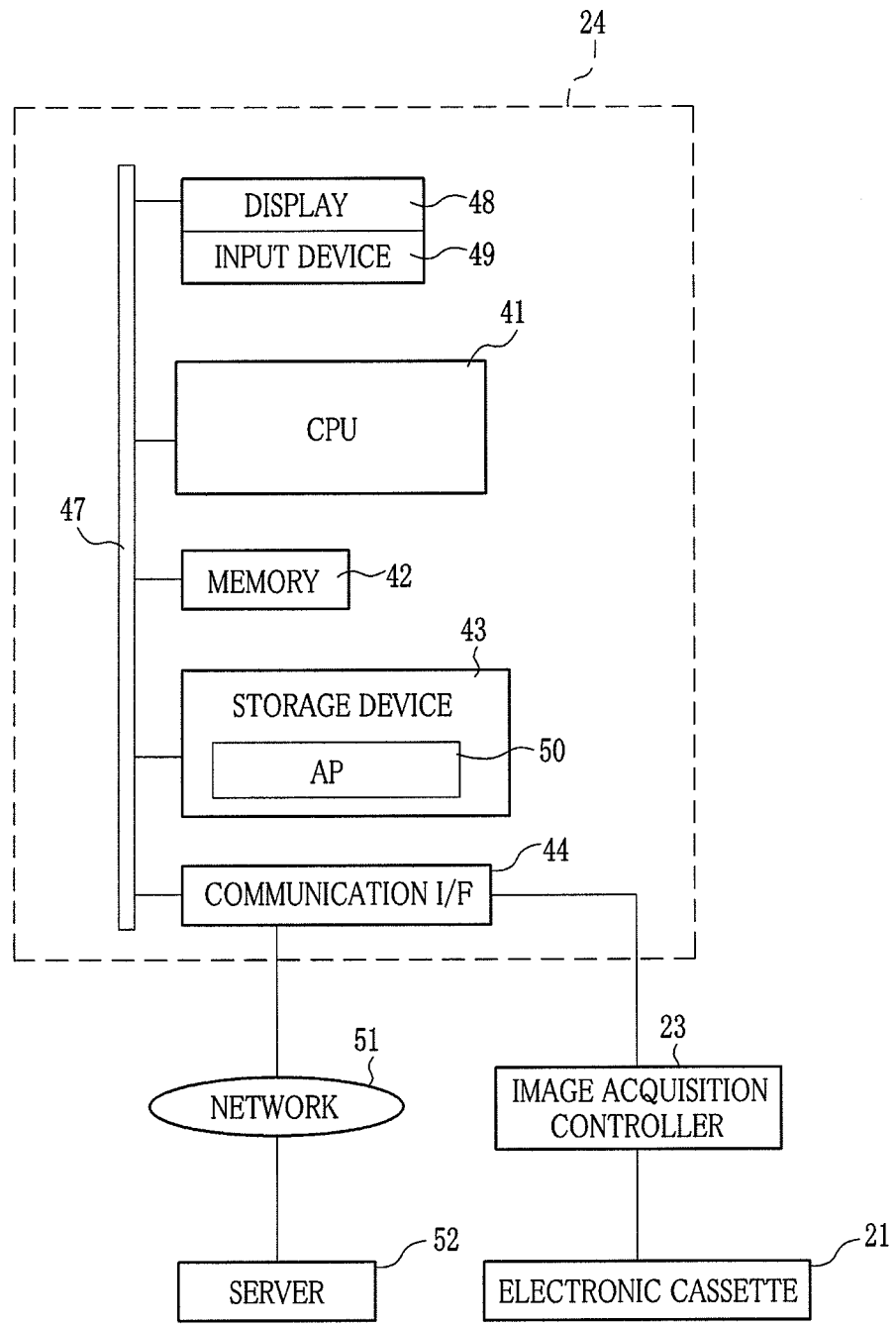
FIG. 7 is a diagram schematically illustrating a console of the radiography system.

As shown in FIG. 7, the console 24 is configured based on a computer, such as a personal computer or a workstation, installing control programs like an operating system and application programs (AP) 50 for actuating the computer to serve as the console 24.

The console 24 includes a CPU 41, a memory 42, a storage device 43, a communication interface (I/F) 44, a display device 48, and an input device 49. These components are connected to each other via a data bus 47. The input device 49 includes a keyboard or a mouse. The input device 49 may include a touch panel that is integrated into the display device 48.

The storage device 43 may for example be a hard disc drive built in the main body of the console 24. The storage device 43 stores the control programs and the application programs 50 that may include software for console.

The memory 42 is a work memory for the CPU 41 to execute processing. The CPU 41 carries out procedures according to the control program loaded from the storage device 43 to the memory 42, to totally control the respective components of the computer while. The communication interface 44 has a network interface that controls data transmission between the console 24 and a network 51, such as LAN. Over the network 51, the console 24 communicates with a server 52, including an image database server, RIS and HIS. The communication interface 44 also includes an interface for communication between the console 24 and the communicator 29 of the electronic cassette 21 through the image acquisition controller 23.

The software for console includes programs for actuating the computer to display the examination orders or radiographs from the electronic cassette 21 on the display device 48, process the radiographs, or determine acquisition settings according to the acquisition order.

Figure 8:
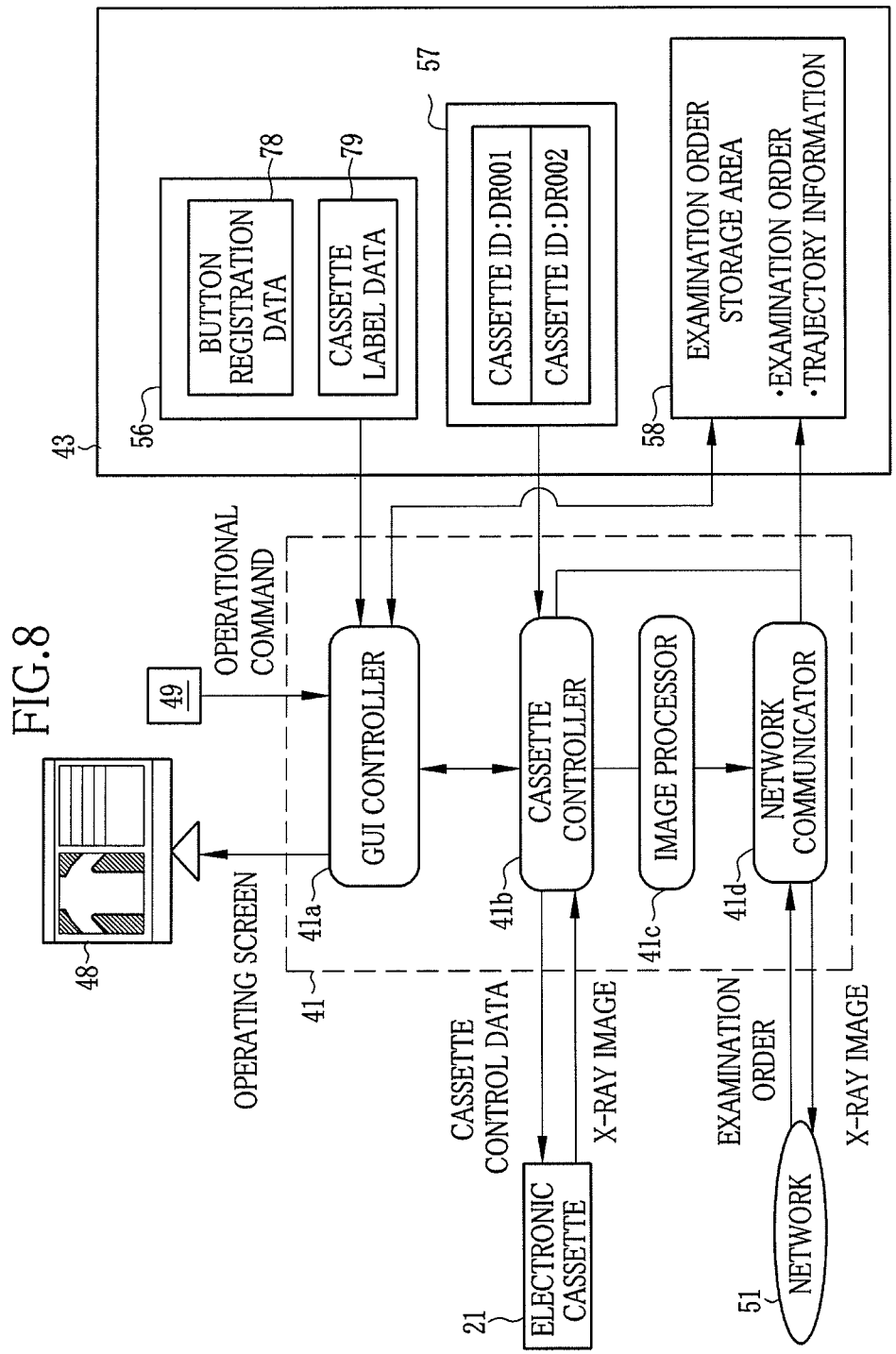
FIG. 8 is an explanatory diagram illustrating the function of the console.

As shown in FIG. 8, when the software for console gets activate, the CPU 41 begins to cooperate with the memory 42 to function as a GUI controller 41a, a cassette controller 41b, an image processor 41c and a network communicator 41d. The GUI controller 41a is an input-output controller for controlling data output to the display device 48 and data input from the input device 49, so as to output radiographic image data acquired by the electronic cassette 21 or operating screens based on graphical user interfaces (GUI) to the display device 48 and to receive operational commands that may be entered on the operating screens using the input device 49.

Figure 10:
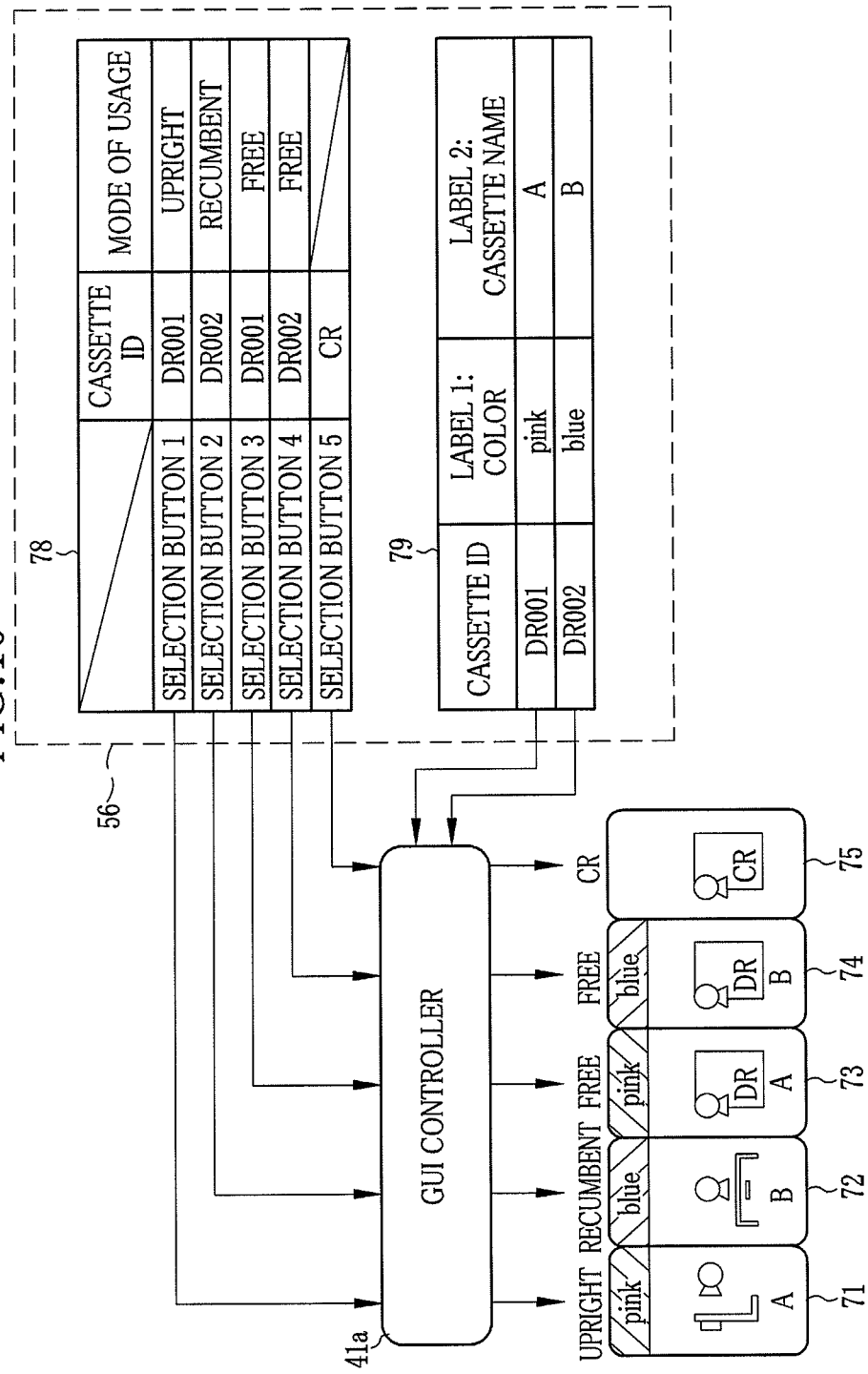
FIG. 10 is an explanatory diagram illustrating a method of producing selection buttons.

The storage device 43 stores data for the operating screens 56, including button registration data 78 and cassette label data 79 (see FIG. 10). The GUI controller 41a reads out the data for the operating screens 56 from the storage device 43 to produce an operating screen on the display device 48.

The cassette controller 41b communicates with the electronic cassette 21 via the communication interface 44 and the image acquisition controller 23, to control the electronic cassette 21. The cassette controller 41b outputs instructions to power the electronic cassette 21 on and off, instructions to switch over the electronic cassette 21 between the power-saving mode and the imaging standby mode, and control data received by the GUI controller 41a, including acquisition settings.

The console 24 is previously registered with more than one cassette 21 that is controllable by the console 24, and data of the registered cassettes 57 is stored in the storage device 43. The registered cassette data 57 includes specification data of the individual cassette 21, such as the cassette ID, the size of imaging plane of the cassette, and the communication format (wireless or wired). In the illustrated example, two cassettes 21 with the cassette IDs "DR001" and "DR002" are registered.

The cassette controller 41b determines the cassette ID of one cassette 21 that is selected to be used for imaging with reference to selection data input through the GUI controller 41a. Then the cassette controller 41b communicates with the determined cassette 21.

The cassette controller 41b also receives the image data of radiographs from the electronic cassette 21 and transfers it to the image processor 41c. The image processor 41c processes the radiographic image data for various kinds of image processing, such as sharpness-correction and frequency processing.

The network communicator 41d communicates with the server 52 via the communication interface 44 and the network 51, to receive orders for examination from the RIS or HIS or send the radiographic image data to the image database server. The storage device 43 is provided with an examination order storage area 58 so that the network communicator 41d will store the received examination orders in the examination order storage area 58.

The examination order storage area 58 stores trajectory information on each examination order in addition to the data of the examination orders. The trajectory information includes the cassette ID of the electronic cassette 21 that was used for imaging, the acquisition settings on the electronic cassette 21, the mode of usage of the electronic cassette 21 (whether it was used in a radiographic stand or table or independently), and the filename of the acquired radiographic image data. The trajectory information is recorded in association with each acquisition order contained in the examination order. The trajectory information may be recorded by the GUI controller 41a or the cassette controller 41b.

Figure 9:
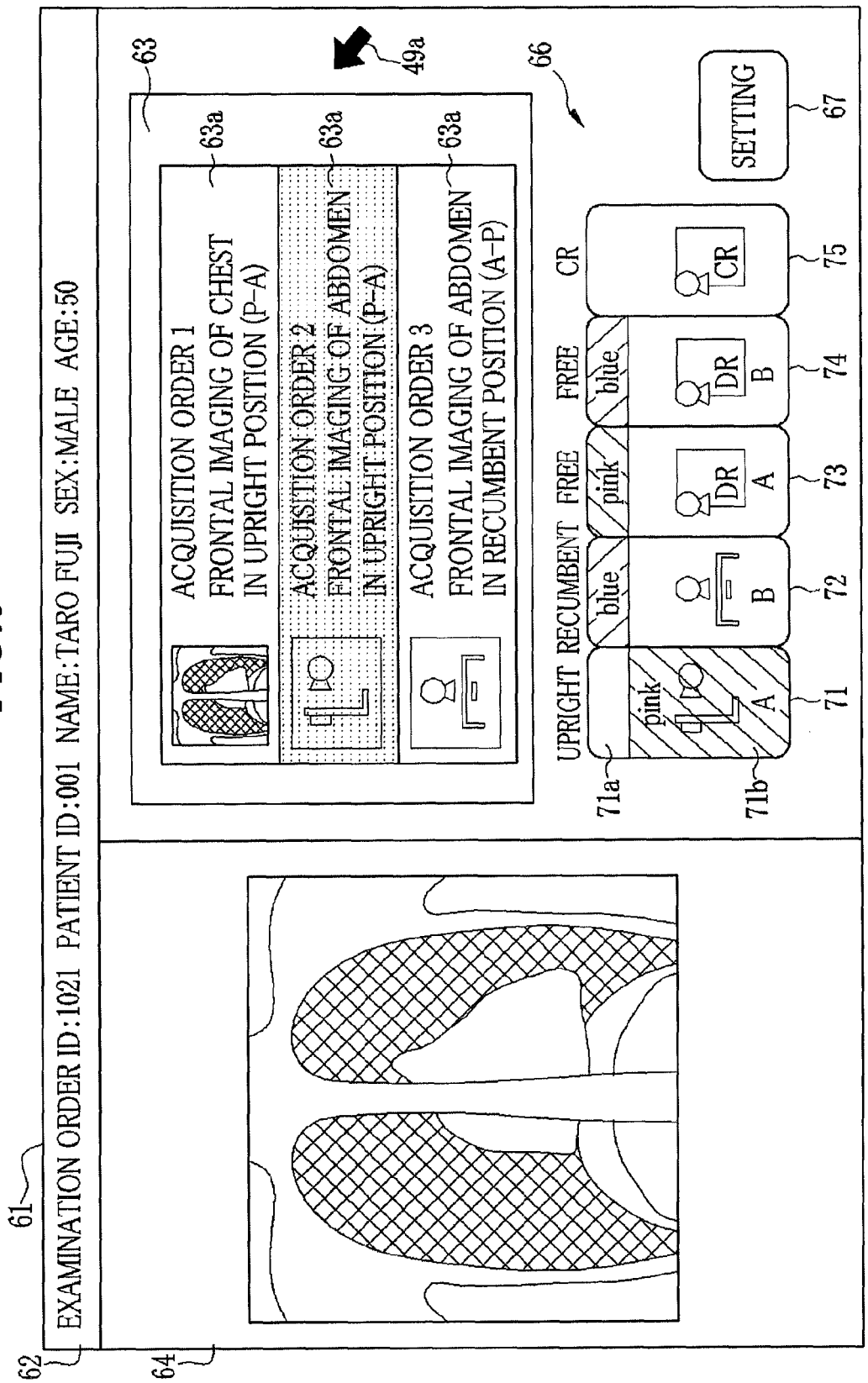
FIG. 9 is an explanatory diagram illustrating an operating screen.

Referring to FIG. 9, an example of an examination order display screen 61 is illustrated. The examination order display screen 61 is one of the operating screens produced by the GUI controller 41a, and displays the content of one examination order selected from among already received examination orders.

The examination order display screen 61 includes a patient information display section 62 displaying information on a patient, such as the examination order ID, the patient ID, and the name, sex and age of the patient. The examination order display screen 61 also includes an acquisition order display section 63 displaying acquisition orders contained in one examination order, and an image display section 64 displaying the acquired radiograph. Below the acquisition order display section 63 is provided a cassette selecting section 66 for selecting one from among the registered cassettes. Designated by a reference numeral 67 is a setting button for making various kinds of settings.

In the acquisition order display section 63, one or more acquisition orders contained in the examination order are displayed in a list. In FIG. 9, the examination order display screen 61 displays the examination order containing the first to third acquisition orders shown in FIG. 6. One display segment 63a of the acquisition order display section 63 displays the procedure information on the radiographic procedure designated by one acquisition order, e.g. "frontal chest radiograph in the standing position (P-A)".

When one of the display segments 63a is selected by putting a mouse pointer 49a and clicking the mouse of the input device 49 thereon, the acquisition order displayed in this display segment 63a is selected. At that time, the selected display segment 63 is highlighted to discriminate it from other acquisition orders. The illustrated example shows that the second acquisition order is selected.

When one acquisition order has been executed, the display segment 63a for the executed acquisition order will display a thumbnail or scale-reduced image of the acquired image in a left marginal position. In the display segment 63a of the unexecuted acquisition order, a symbol indicating the designated radiographic procedure, e.g. the upright position or the laying position, is displayed instead. In the illustrated example, the first acquisition order has been executed, and the thumbnail of the acquired image is displayed in the corresponding display segment 63a, whereas the second and third acquisition orders have not yet been executed, and symbols indicating the designated radiographic procedures are respectively displayed in the corresponding display segments.

The image display section 64 displays the latest image among those acquired by the electronic cassette 21. In the illustrated example, the image displayed in the image display section 64 corresponds to the first acquisition order. The image display section 64 may also display a selected one of those images which have already been captured.

The cassette selecting section 66 is provided with a plurality of selection buttons 71 to 75, the buttons 71 to 74 for selecting electronic cassettes 21 and the button 75 for selecting an IP or CR cassette.

In order to acquire an image by one electronic cassette 21 in response to an acquisition order, a corresponding one of the selection buttons 71 to 74 is selected by placing and clicking the pointer 49a thereon to select the one electronic cassette 21 according to the content of the acquisition order. A cassette ID is assigned to each selection button 71 to 74.

Selection data of the electronic cassette 21 by the selection buttons 71 to 74 is fed to the cassette controller 41b through the GUI controller 41a. The cassette controller 41b determines the cassette ID of the selected cassette 21 by the selection data, and communicates with the selected cassette 21. The GUI controller 41a accesses the examination order storage area 58 to record the selection data of the electronic cassette 21 in association with the designated acquisition order as a new set of trajectory information.

To acquire an image by an IP cassette in place of the electronic cassette 21, the selection button 75 is selected. Unlike the electronic cassette 21, the IP cassette cannot communicate with the console 24. Therefore, the selection data of the IP cassette is not fed to the cassette controller 41b, but the GUI controller 41a records the selection data of the IP cassette in association with the designated acquisition order as a new set of trajectory information.

In addition, the selection buttons 71 to 74 are provided not only for the respective electronic cassettes 21 but also for different modes of usage of each cassette, so that each selection button may designate one cassette and a mode of usage of the cassette. In other words, multiple selection buttons are provided for one electronic cassette 21 in order to select different modes of usage of each cassette 21. As shown in FIG. 8, two electronic cassettes 21 with the cassette ID "DR001" and "DR002" have been registered in the illustrated example.

Providing that the cassette 21 having the ID "DR001" is named "A" and tagged with the label 33A, and that the cassette 21 having the ID "DR002" is named "B" and tagged with the label 33B, these cassettes 21 will be discriminated by the reference numerals 21A and 21B respectively.

The selection button 71 and the selection button 73 are associated with the same cassette ID "DR001". The selection button 71 is selected to use the electronic cassette 21A in the radiographic stand 31, whereas the selection button 73 is selected to use the electronic cassette 21A independently, i.e. freely from the radiographic stand. Hereinafter, the mode of usage of the cassette 21 in an independent style will be referred to as free position imaging.

When the selection button 71 is selected, the GUI controller 41a inputs the selection data to the cassette controller 41b and records data of the designated mode of usage, i.e. the upright position imaging in this case, in the examination order storage area 58 in association with the acquisition order as the trajectory information. When the selection button 73 is selected, data indicating that the free position imaging is designated as the mode of usage is recorded as the trajectory information.

Likewise, the selection button 72 and the selection button 74 are associated with the same cassette ID "DR002". The selection button 72 is selected to use the electronic cassette 21B in the radiographic table 32, whereas the selection button 74 is selected to use the electronic cassette 21B for the free position imaging. When the selection button 72 is selected, data indicating that the recumbent position imaging is designated as the mode of usage is recorded as the trajectory information. When the selection button 74 is selected, data indicating that the free position imaging is designated is recorded as the trajectory information.

Because the mode of usage of the electronic cassette 21 is an important factor to be recorded as examination data, it is advantageous to provide the selection buttons for respective modes of usage of each registered cassette so as automatically to record the designated mode of usage as the trajectory information. Thus, the mode of usage of the electronic cassette 21 will be recorded without failure.

As described so above, a couple of electronic cassettes 21 are often provided in one x-ray room such that one is usually mounted in one radiographic stand 31 and the other is usually mounted in one radiographic table 32, and that either of these cassettes 21 may be removed from the radiographic stand or table 31 or 32 to use it for the free position imaging. In practice, in order to prevent confusion between the different cassettes 21A and 21B, each cassette 21 is usually fixedly assigned to a particular radiographic stand or table. For example, the cassette 21A is determined be mounted in the radiographic stand 31, and the electronic cassette 21B is determined to be mounted in the radiographic table 32.

Taking this practice into consideration, the present embodiment provides two selection buttons 71 and 73 for one electronic cassette 21A for the upright position imaging in the radiographic stand 31 and the free position imaging, as well as two selection buttons 72 and 74 for the other electronic cassette 21B for the recumbent position imaging in the radiographic table 32 and the free position imaging.

The selection buttons 71 to 74 are provided with symbols indicating the assigned modes of usage, the symbol on the selection button 71 representing a radiographic stand and an x-ray source, the symbol on the selection button 72 representing a radiographic table and an x-ray source, and the symbols on the selection buttons 73 and 74 representing a cassette and an x-ray source. Letters "DR" in the symbol on the selection buttons 73 and 74 are representing the electronic cassette 21, while letters "CR" in a symbol on the selection button 75 is representing the IP or CR cassette.

In addition to the symbol, literal information, such as "upright", "recumbent" or "free", is displayed above each selection button 71 to 74. The literal information may be displayed inside the selection buttons 71 to 74.

The symbols and the literal information show the operator or radiologist the modes of usage of the cassettes 21A and 21B selectable by the respective selection buttons 71 to 74. Thus the radiologist may select one of the selection buttons 71 to 74 according to the radiographic procedure of one acquisition order designated in the acquisition order display section 63.

The console 24 also has a function to select any of the selection buttons 71 to 74 automatically on the basis of the designated acquisition order. The GUI controller 41a monitors which of the acquisition orders is currently designated on the list in the acquisition order display section 63. When one acquisition order is designated, the GUI controller 41a refers to the procedure information contained in the designated acquisition order, to determine the designated radiographic procedure, such as the upright position, the recumbent position, or the free position. According to the designated procedure, the console 24 activates a corresponding one of the selection buttons 71 to 74 to automatically select an appropriate cassette 21 for the imaging.

For example, when the second acquisition order is designated by the pointer 49a in the acquisition order display section 63, the GUI controller 41a determines with reference to the procedure information of the second acquisition order that the second acquisition order requests an imaging in the upright position, so that the selection button 71 for the upright position imaging is automatically set in the selected condition. Thus an appropriate one of the registered cassettes 21 is automatically selected in combination with its mode of usage according to the content of the designated acquisition order. This configuration will prevent failure in confirming the content of the acquisition order and secure correct selection of the electronic cassette 21 and its mode of usage according to the acquisition order.

Moreover, the selection buttons 71 to 74 are configured to help the operator confirm that the electronic cassette 21 positioned relative to the target site of the subject H coincides with the electronic cassette 21 as selected on the console 24. The selection buttons 71 to 74 are provided with the same labels as recorded on the labels 33 put on the corresponding cassettes 21.

The selection buttons 71 and 73, which are assigned to the electronic cassette 21A, have the same label as the label 33A of the electronic cassette 21A. In the present example, the label 33A is colored pink and recorded with the cassette name "A" (see FIG. 3). Corresponding to the label 33A, the selection buttons 71 and 73 are colored pink and provided with the cassette name "A" as the literal information.

Likewise, the selection buttons 72 and 74, which are assigned to the electronic cassette 21B, have the same label as the label 33A of the electronic cassette 21A. Since the label 33B is colored blue and recorded with the cassette name "B" (see FIG. 3), the selection buttons 72 and 74 are colored blue and provided with the cassette name "B" as the literal information.

Through comparison of the labels on the selection buttons 71 to 74 with the labels 33 on the electronic cassettes 21, the radiologist can make sure to position the same cassette 21 as selected on the console 24 for imaging of the target site of the designated subject H in the designated x-ray room.

The selection buttons 71 to 74 may be displayed in two colors: a basic or first color that is common to these buttons 71 to 74 and a second color corresponding to the label color. The basic color may for example be black. Then the selection buttons 71 and 73 are displayed in black and pink, whereas the selection buttons 72 and 74 are displayed in black and blue. In the drawings, the hatched areas in the selection buttons 71 to 74 correspond to the label-colored areas. Note that the words "pink" and "blue" written in the hatched areas are just indicating the color of each label for convenience in the white-and-black drawings. Namely, these words are not actually displayed on the selection buttons.

Taking the selection button 71 for example, it is divided into upper and lower halves 71a and 71b. While the button 71 is not selected, the upper half 71a is displayed in the label color, and the lower half 71b is displayed in the basic color. When the button 71 is selected, the lower half 71b is displayed in the label color, and the upper half 71a is displayed in the basic color. Thus, the first and second colors of the selection buttons 71 to 74 are replaced with each other when the selection button 71, 72, 73 or 74 is selected.

In FIG. 9, the selection button 71 is shown in the selected condition, wherein the lower half 71b is displayed in the label color, pink, and the upper half 71a is displayed in the basic color, black. The selection buttons 72 to 74 are shown in the not-selected condition having the inverse color display to the selected button 71.

This way, the respective selection buttons 71 to 74 always display their labels, color and cassette name, regardless of whether selected or not, and the discrimination between the selected condition and the not-selected condition is displayed by interchanging the colors between the upper and lower halves of each button. Because the labels are displayed continuously on the selection buttons 71 to 74, the operator can check the label of the electronic cassette 21 after it is positioned for imaging of the subject H, and then select one selection button that has the corresponding label to the label of the positioned cassette 21. This is more convenient in comparison with a case where the label is not displayed on the selection button until it is selected.

Referring to FIG. 10, the data for the operating screens 56, which is stored in the storage device 43, is illustrated. The data 56 includes the button registration data 78. The button registration data 78 is previously registered data for defining the assignment of the selection buttons 71 to 75 to the cassettes, including the assignment of the selection buttons 71 to 74 to the cassette IDs and the modes of usage of the electronic cassettes 21. That is, the button registration data 78 is the claimed second correspondence data indicating the correspondence of the selection buttons 71 to 74 with the modes of usage of the electronic cassettes 21. In the button registration data 78, first to fifth selection buttons correspond to the selection buttons 71 to 75.

Concerning the selection button 75 (the fifth selection button) for the IP cassette, the button registration data 78 merely defines that this is for selecting the IP cassette (CR), and does not define any cassette ID or mode of usage. The GUI controller 41a refers to the procedure information of the designated acquisition order and the button registration data 78 when selecting the selection button automatically according to the acquisition order.

The data for the operating screens 56 also include the cassette label data 79, which indicates the correspondence of the cassette IDs given to the respective cassettes 21 with the labels on the cassettes 21. Namely the cassette label data 79 is the claimed first correspondence data. In the present embodiment, the cassette label data 79 defines the label color (first label element) and the cassette name (second label element) in combination with each cassette ID.

The GUI controller 41a reads out screen data that defines a basic form of the examination order display screen 61 and assigns the cassette IDs and the modes of usage to the respective selection buttons 71 to 74 in the basic form with reference to the button registration data 78. Then the GUI controller 41a reads out the labels corresponding to the respective cassette IDs from the cassette label data 79 and displays the corresponding labels on the selection buttons 71 to 74.

In FIG. 11 is illustrated a label setting screen 81 for setting or modifying the cassette label data 79. The label setting screen 81 is provided with setting boxes 82 and 83 for setting or modifying the label color (the first label element) and the cassette name (the second label element), respectively. When an arrow of the setting box 82 or 83 is clicked on by the pointer 49a, a pull-down menu 82a or 83a is displayed downwards of the box 82 or 83, to show the candidates. The pull-down menu 82a shows available label colors, including an option for setting no color. The pull-down menu 83a shows available cassette names, including an option for setting no name and an option for inputting an arbitrary letter string.

The GUI controller 41a accepts the label modifying operation on the label setting screen 81 to modify the cassette label data 79 in the storage device 43. Manually modifiable cassette label data permits flexible application to individual medical facilities.

Now the operation of the radiographic system 10 will be described with reference to FIGS. 12 to 15. To make an x-ray examination by the system 10, the operator or radiologist operates the console 24 to select an examination order. Then the GUI controller 41a produces the examination order display screen 61 and displays it on the display device 48, as is shown in FIG. 9.

The selection buttons 71 to 75 are displayed with the labels corresponding to the assigned electronic cassettes 21A and 21B, the labels being defined by the button registration data 78 and the cassette label data 79. When one acquisition order is designated in the acquisition order display section 63, the GUI controller 41a automatically selects one selection button that corresponds to the procedure designated by the acquisition order.

Data of the selected selection button is fed to the cassette controller 41b so that the cassette controller 41b determines the electronic cassette 21 having the cassette ID corresponding to the selected button, and starts communicating with the determined electronic cassette 21. The cassette controller 41b instructs the selected electronic cassette 21 to proceed to the imaging standby mode and, if acquisition settings are entered, the cassette controller 41b sends these acquisition settings to the selected electronic cassette 21.

As shown in FIG. 12, when the selection button 71 for the upright position imaging is automatically selected, the color display condition of the selection button 71 is changed to indicate that the selection button 71 is now selected. The radiologist checks the display segment 63a of the designated acquisition order to confirm that the upright position imaging is designated and the corresponding selection button 71 to this procedure is selected.

Then the radiologist places the subject or patient H in front of the radiographic stand 31 and adjusts the relative position of the electronic cassette 21A, mounted in the radiographic stand 31, to the subject H by operating the radiographic stand 31. At the same time, the radiologist checks the label 33A on the electronic cassette 21A, i.e. the label color and the cassette name on the label 33A.

Then the radiologist checks the label displayed on the selected button 71 to confirm that the label on the selection button 71 has the same color and the same cassette name as the label 33A on the electronic cassette 21A, i.e. "pink" and "A" in the present example. Through the comparison of the label 33 on the electronic cassette 21 with the label on the selected selection button, the radiologist can check whether the electronic cassette 21 positioned to the subject H coincides with the electronic cassette 21 that is selected on the console 24.

Thus the present invention makes it easier and securer to make the above-described confirmation of the electronic cassette or discriminate the individual electronic cassettes even between those having an identical appearance like the electronic cassettes 21A and 21B. Especially for those electronic cassettes which have the same size as film cassettes and IP cassettes, like the electronic cassettes 21A and 21B, the present invention is useful because their appearances are closely similar to each other even between different models. The present invention is still more useful for wireless electronic cassettes like the electronic cassettes 21A and 21B because it is impossible to check the connection of the wireless electronic cassettes to the console 24 by tracing connection cables.

Moreover, the cassette labels including colors as one element in addition to the cassette names depicted as letter strings facilitate instinctive identification of the cassettes as compared to those labels having literal information only. Therefore, the colored labels are useful for preventing incorrect imaging due to confusion between the electronic cassettes 21 or wrong operation on the console 24.

In addition to the above feature, unlike the conventional film cassettes or IP cassettes, the electronic cassettes 21 can transmit the acquired image data over a wireless or wired communication network. For this reason, the electronic cassettes 21 may be used in the different manner from the film cassettes or IP cassettes, as set forth below.

In the radiography using the film cassettes or IP cassettes, the radiologist brings a number of film cassettes or IP cassettes required for one examination from the storage into the x-ray room in advance to the examination or radiographic imaging, and takes the used cassettes out of the x-ray room after the examination. This is because the film cassettes must be processed for development and the IP cassettes must be put in a data reading device for reading acquired image data. Therefore, concerning the film cassettes and IP cassettes, the trouble of using wrong cassettes can hardly occur.

In contrast to this, the electronic cassettes, being capable of transmitting image data, can be used repeatedly for many examinations without the need for bringing them out of the x-ray room. As described above, one electronic cassette is usually loaded in a radiographic stand and used for acquiring many radiographs in this position, but may also be used separately from the radiographic stand. Therefore, confusion or misplacement of the electronic cassettes can occur when the cassette is reloaded in the radiographic stand or table. The problem of confusing the cassettes is therefore specific to the electronic cassettes that have the function to transmit the image data and hence need not to be brought into and out of the x-ray room.

As described above, the electronic cassettes 21 have the same or similar appearance to each other although they can be identified with the cassette IDs on the computer system like the console 24. Therefore, the radiologist can easily get uncertain of the cassette ID of the electronic cassette 21 presently loaded in the radiographic stand or table. If the cassette ID of the presently loaded electronic cassette 21 does not coincide with the cassette ID selected on the console 24, no image will be acquired even while x-rays are projected from the x-ray source. Such erroneous imaging will dose the patient H uselessly.

The present invention is very effective for solving the above described problem that can occur in the advanced electronic cassettes which are provided with the image transmission device.

If just two electronic cassettes are registered for use in an x-ray room, like the cassettes 21A and 21B in the above described embodiment, the operator may also identify the one cassette positioned to the subject H by checking the label 33 of the other cassette that is not positioned to the subject H. For example, in a situation where the radiographic table 32 is located nearer to the console 24 than the radiographic stand 31, the electronic cassette 21A is mounted in the radiographic stand 31, the electronic cassette 21B is mounted in the radiographic table 32, the selection button 71 for the upright position imaging is selected on the console 24, and the subject H stands at the radiographic stand 31, the radiologist can compare the label on the selection button 71 with the label 33B on the electronic cassette 21B that is nearer to the console 24 to confirm that the electronic cassette 21A mounted in the radiographic stand 31 and positioned to the subject H coincides with the electronic cassette 21A that is selected by the selection button 71 on the console 24. The same applies to the situation where the electronic cassette 21B is detached from the radiographic table 32 and placed nearer to the console 24 than the electronic cassette 21A that is designated by the acquisition order.

Since the labels 33 are put on multiple sides of the electronic cassette 21, it is easy to check any of the labels 33 in various positions of the electronic cassette 21 regardless of whether it is mounted in the radiographic stand or table 31 or 32 or separated therefrom.

Moreover, the selection buttons 71 to 74 also display the corresponding modes of usage of the electronic cassette 21, which facilitates and ensures the discrimination between the upright position and the recumbent position, as shown in FIG. 12, and the free or independent position of the electronic cassette 21, like as shown in FIG. 13. When the electronic cassette 21B is used for the free position imaging, as is shown in FIG. 13, the label color "blue" and the cassette name "B" of the label 33B on the electronic cassette 21B should be compared to those of the label displayed on the selection button 73 for the free position imaging by the electronic cassette 21B.

There may be a case where it is impossible to execute the radiographic procedure designated by the acquisition order. For example, as shown in FIG. 14, when the patient H lies on a stretcher 86 and cannot keep standing in the upright posture while the acquisition order designates the upright position imaging, the radiologist may decide to execute the free position imaging instead. Then, the radiologist removes, for example, the electronic cassette 21B from the radiographic table 32 and squeezes the electronic cassette 21B into between the stretcher 86 and the patient H, to acquire images in this position.

Figure 15A:
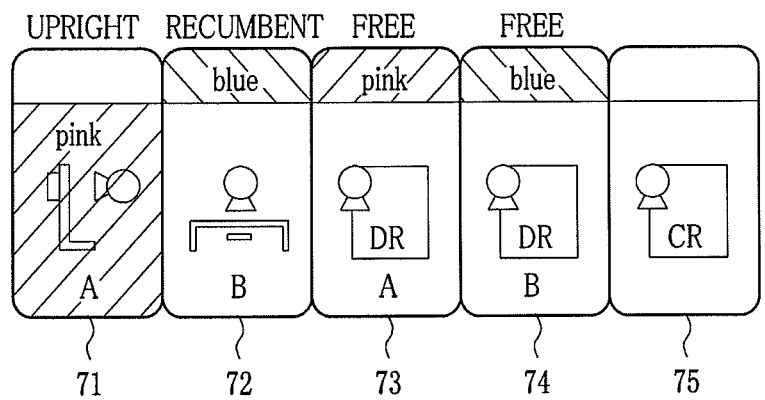
FIGS. 15A and 15B are explanatory diagrams illustrating a change in selection of the selection buttons.

In that case, according to the acquisition order designating the upright position imaging, the selection button 71 for the upright position is automatically selected on the console 24, as shown in FIG. 15A. After removing the electronic cassette 21B from the radiographic table 32, the radiologist checks the label 33B on the electronic cassette 21B (the label color "blue" and the cassette name "B") and selects the selection button 74 that is displayed in blue with the cassette name "B" among the selection buttons 73 and 74 for the free position imaging.

Since the selection buttons 71 to 74 continue to display the labels regardless of whether they are selected or not, the radiologist can find the button to be selected from among the selection buttons 71 to 74 after checking the label 33 on the electronic cassette 21 that has been positioned to the subject H.

Figure 15B:
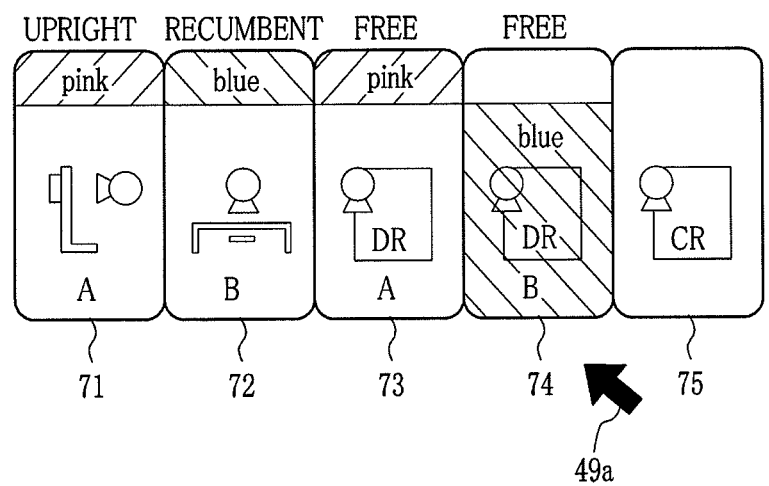

When the selection button 74 is selected, the selection button 74 is switched to the selected condition, as shown in FIG. 15B. Then the radiologist reconfirms that the label of the selected button 74 coincides with the label 33B on the positioned cassette 21B before starting the image acquisition. The GUI controller 41a records data reporting the change of radiographic procedure by the selection of the selection button 74 as trajectory information of the acquisition order.

Thus, the selection buttons 71 to 74 displaying the modes of usage in addition to the labels are effective to prevent the wrong selection even while the electronic cassette 21 or its mode of usage is being changed from the designation by the acquisition order. Thus, the present invention is preferably applicable to the electronic cassettes 21 that may be used flexibly in various ways.

Figure 16:
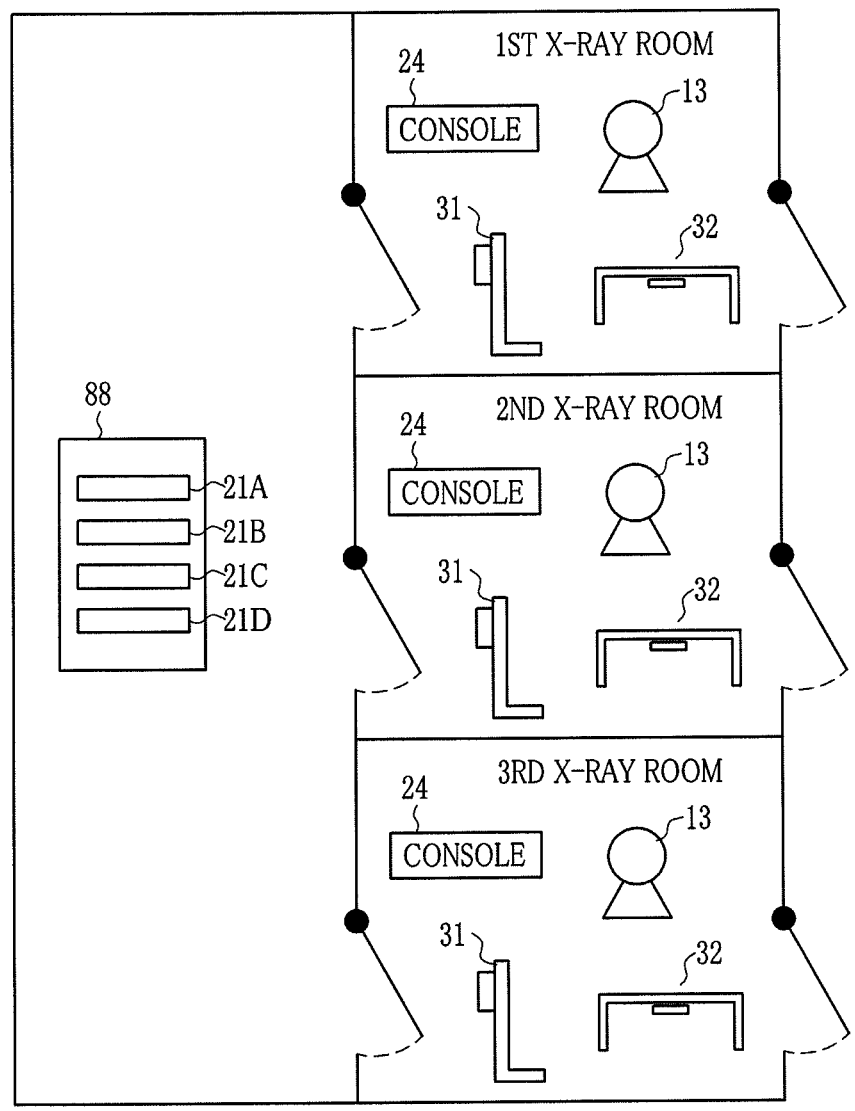
FIG. 16 is an explanatory diagram illustrating a case where the electronic cassettes are used in several x-ray rooms.

Furthermore, it is preferable to configure the radiographic system 10 to be capable of revising the button registration data 78 especially when it is applied to such medical facilities that have a plurality of x-ray rooms, as shown in FIG. 16, and a plurality of electronic cassettes are selectively used in any of these x-ray rooms. In the example of FIG. 16, first to third x-ray rooms adjoin and have a front entrance for the patient H and a rear entrance for the radiologist. The rear entrances of the x-ray rooms are connected through a corridor.

A rack 88 holding the electronic cassettes 21A to 21D is placed on the corridor. The electronic cassettes 21A to 21D are tagged with different labels 33. A console 24, an x-ray source 13, a radiographic stand 31 and a radiographic table 32 are installed in each x-ray room, so that the electronic cassettes 21A to 21D may be selectively used in the designated mode in the designated x-ray room.

In this situation, each console 24 is preferably provided with the function to revise the button registration data 78. Then, the radiologist can revise the button registration data 78 on the console 24 in one x-room according to the label 33 on the cassette that is selected for use in the one x-room. For example, if the electronic cassettes 21 selected from among the electronic cassettes 21A to 21D vary from day to day even in the same x-ray room, the radiologist can flexibly revise the button registration data 78 to adapt the labels on the selection buttons 71 to 74 of the console 24 to the labels on the selected cassettes 21.

Because the electronic cassettes 21 are expensive, the cost of installing the same number of electronic cassettes 21 as the number of radiographic stands and tables 31 and 32 will be a heavy economic burden to medical facilities. Owing to the capability of revising the button registration data 78, the radiographic system 10 of the present invention enables the medical facilities to manage with less electronic cassettes 21 than the radiographic stands and tables 31 and 32 in the manner as described with reference to FIG. 16. Therefore, the radiographic system 10 will be of great economic advantage to the medical facilities.

It should be appreciated that the functions of the console 24 and the style of the operating screen have been described just for illustrative purpose in the above embodiment and may be modified in various ways. For example, the console 24 may not necessarily have the function to select a button automatically according to the acquisition order or the function to revise the button registration data 78, although the console 24 preferably has these functions because of the above described effects.

How many selection buttons should be provided and which mode of usage should be assigned to each selection button are also modifiable according to the demand. For example, the selection button 71 for the upright position imaging and the selection button 72 for the decumbent position imaging may be provided for each electronic cassette available to the system 10, in the same way as the selection buttons 73 and 74 for the free position imaging are provided for the respective electronic cassettes 21A and 21B. Alternatively, it is possible to assign only the cassette ID to each selection button without assigning the mode of usage. In that case, the selection buttons may be provided in the same number as the number of cassette IDs, i.e. that of available electronic cassettes 21.

Figure 17A:
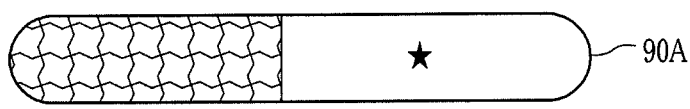
FIGS. 17A, 17B and 17C are explanatory diagrams illustrating cassette labels each consisting of a pattern and a symbol.
Figure 17B:
Figure 17C:
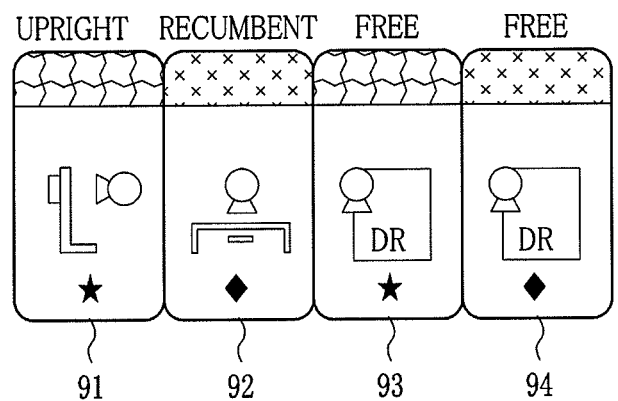

In the above embodiment, the cassette label includes the label color as one element. Instead of or in addition to the label color, the cassette label may include a pattern, as shown for example by labels 90A and 90B in FIGS. 17A and 17B. Moreover, in place of a letter or letter string, a symbol, a mark or numerals may be included in the cassette name. As an example of the symbol, a star or a diamond may be recorded on the label 90A or 90B respectively. Then the corresponding patterns and symbols should be displayed on individual selection buttons 91 to 94, as shown in FIG. 17C.

Although each cassette label is provided as a combination of multiple elements, such as color and letter or pattern and symbol, in the above embodiments, the cassette label may include at least one element among colors, letters, and patterns. Most preferably, the cassette labels include colors, because colors are most instinctively perceivable among other elements.

In the above embodiments, the selection buttons 71 to 74 always display the labels and interchange the label colors between the upper and lower halves of the selected button to show that the button having the inverted color display is currently selected among these selection buttons 71 to 74. In an alternative, which selection button is selected may be displayed by changing the position, the shape or the size of any label element on the selected button.

The labels may not necessarily be displayed continuously on the selection buttons. Instead, the label may be displayed at least on one selection button when the one selection button is selected. However, for the reason as described above, it is preferable to display the corresponding label continuously on every selection button. In the case where the labels corresponding to the available cassettes are not always displayed on the operating screen, the cassette label of the selected or designated cassette may be displayed outside the selection buttons. For example, a specific section or window may be provided for displaying a label of a corresponding color to a selected one of selection buttons having different colors according to the labels on the assigned cassettes.

Figure 18:
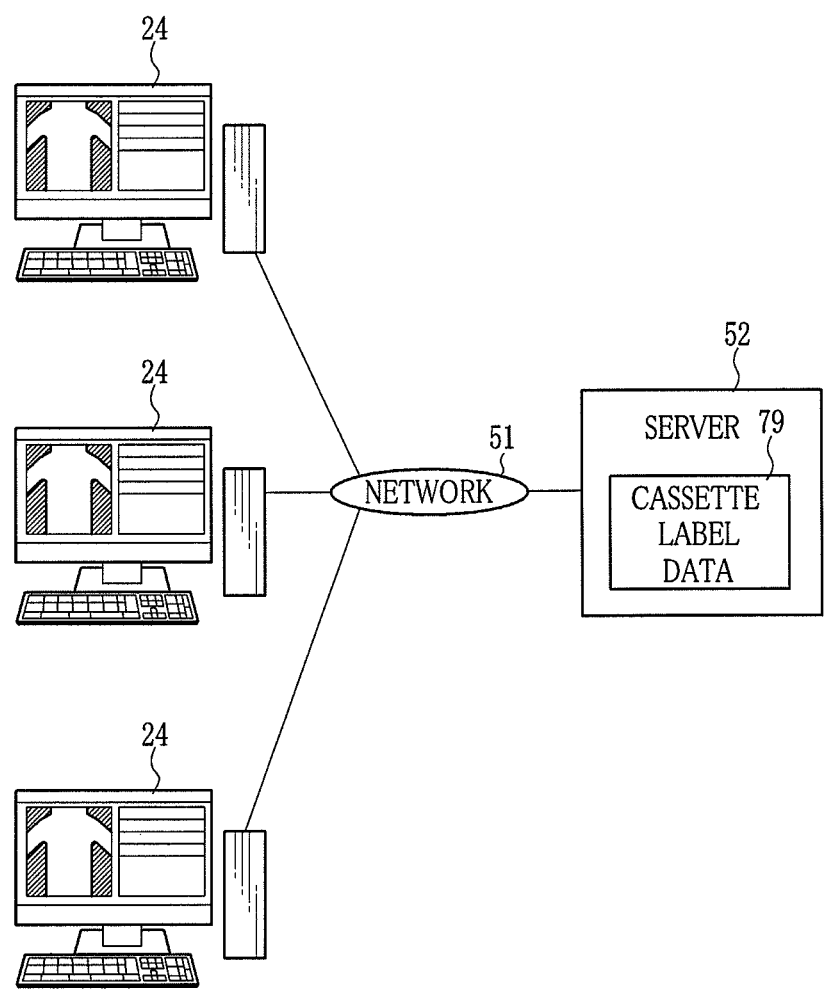
FIG. 18 is an explanatory diagram illustrating an embodiment where a server stores information on the cassette labels.
Figure 19:
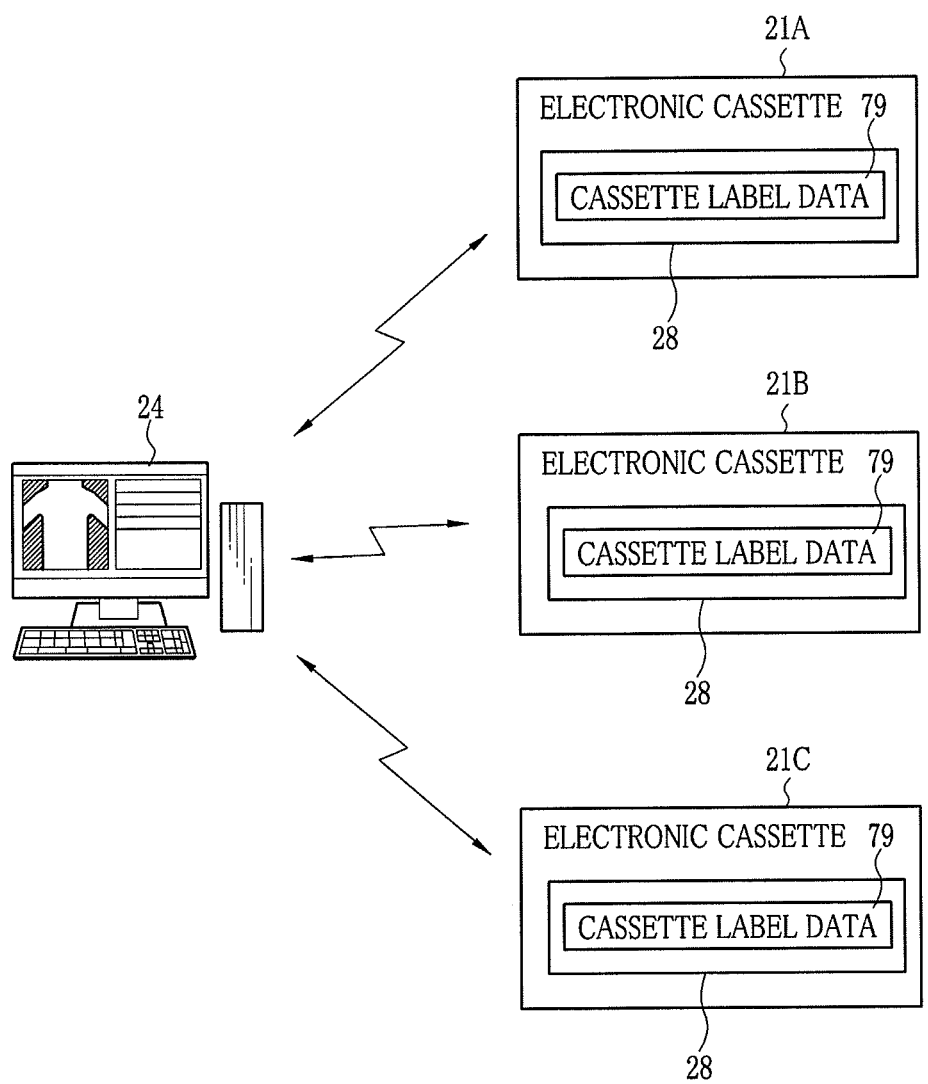
FIG. 19 is an explanatory diagram illustrating an embodiment where a memory of the cassette storages information on the cassette labels.

Moreover, the cassette label data 79 indicating the correspondence of cassette IDs with cassette labels may be stored in other location than the storage device 43 of the console 24. For example, as shown in FIG. 18, the cassette label data 79 may be stored in an external storage device like the server 52, which is communicably coupled to the console 24 over the network 51. Then the console 24 makes an access to the server 52 through the network 51, to obtain the cassette label data 79 on displaying the operating screen. This makes it possible to manage the cassette label data 79 in one location, which facilitates revising the cassette label data 79 and delivering the revised cassette label data 79 to the respective consoles 24.

In the embodiment where the cassette label data 79 is stored in the server 52, the cassette label data 79 may record the correspondence of cassette IDs with cassette labels of all electronic cassettes 21 that can be used in a plurality of x-ray rooms and controlled by a plurality of consoles 24. In that case, each console 24 may readout necessary data from among the cassette label data 79 stored in the server 52. The button registration data 78 may also be stored in the server 52. The button registration data 78 and the cassette label data 79 may be stored in different locations, e.g. one of which is stored in the storage device 43 and the other in the server 52.

Alternatively, the cassette label data 79 may be written in the memory 28 of each electronic cassette 21. Then the console 24 may read out the cassette label data 79 from the memory 28 of the electronic cassette 21. The cassette label data 79 written in the memory 28 of each electronic cassette 21 has to include at least a cassette ID of this cassette 21 and a label that is combined with the cassette ID.

Furthermore, the image acquisition controller 23 may not necessarily be an independent apparatus that is installed separately from the electronic cassette 21 and the console 24. Instead of this, the electronic cassette 21 or the console 24 may be provided with the function of the image acquisition controller 23.

The present invention is not only applicable to x-ray radiography system but also to other radiography systems using other kinds of radioactive rays, e.g. gamma rays.

It should be understood that the embodiments of the present invention have been disclosed for illustrative purposes only. Those skilled in the art will appreciate that various modifications, additions and substitutions are possible without departing from the scope and spirit of the invention as disclosed in the accompanying claims.

What is claimed is:

1. A radiography system comprising:
   an electronic cassette for radiography that has an image detector for detecting radiographic images when irradiated with radioactive rays and a portable housing containing said image detector;
   a label attached to said housing of said electronic cassette, for making said electronic cassette visually distinguishable from other electronic cassettes;
   a console that communicates with a selected one of plurality of said electronic cassettes;
   a first storage device storing first correspondence data that indicates correspondence between the label and a cassette ID given to each of said electronic cassettes, said cassette ID being used by said console for communication with the selected electronic cassette; and
   a control device provided in said console, said control device referring to the first correspondence data to display the label that corresponds to the cassette ID of the selected electronic cassette on a screen, and
   wherein said label includes a color as an element.

2. The radiography system as recited in claim 1, wherein said label further includes at least one of letters, numerals, symbols and patterns as an element.

3. The radiography system as recited in claim 1, wherein said housing is provided with at least a labeling portion on which the label is sealed.

4. The radiography system as recited in claim 1, wherein said control device may display an operating screen using a graphical user interface, said operating screen having a plurality of selection buttons for respective selection of said electronic cassettes, each of said selection buttons being assigned to the cassette ID of one of said electronic cassettes, and the label corresponding to the assigned cassette ID being displayed on each selection button.

5. The radiography system as recited in claim 4, wherein the label is continuously displayed on each of said selection buttons regardless of whether selected or not, and said control device changes the condition of the label displayed on a selected one of said selection buttons to make the selected selection button distinguishable from others.

6. The radiography system as recited in claim 5, wherein each label includes a color as an element, and each of said selection buttons is displayed in first and second colors, the first color being common to all of said selection buttons, the second color being different from one cassette ID to another corresponding to the color of the label, and wherein the first color and the second color are replaced with each other on the selected selection button.

7. The radiography system as recited in claim 4, wherein said electronic cassettes are usable in different modes of usage, including a mode of usage mounted in a radiographic stand or table, and a mode of usage free from the radiographic stand or table, and two or more of said selection buttons are provided for one cassette ID, each of said selection buttons being assigned to one mode of usage.

8. The radiography system as recited in claim 7, wherein the modes of usage assigned to said selection buttons include a mode of usage in which said electronic cassette is mounted in a radiographic stand for imaging in upright position, and a mode of usage in which said electronic cassette is mounted in a radiographic table for imaging in decumbent position.

9. The radiography system as recited in claim 7, wherein said console is provided with an acquisition order receiving device for receiving acquisition orders including data of designating the mode of usage of said electronic cassette.

10. The radiography system as recited in claim 9, further comprising a second storage device for storing second correspondence data indicating correspondence between the modes of usage and said selection buttons, wherein said control device determines one of said selection buttons on the basis of the acquisition order and the second correspondence data, and sets the determined selection button to the selected state to automatically select one electronic cassette to be used for imaging from among said electronic cassettes.

11. The radiography system as recited in claim 1, wherein the first correspondence data is modifiable.

12. The radiography system as recited in claim 11, wherein said console includes a modification accepting device that may access said first storage device to modify the first correspondence data in response to modifying operations.

13. The radiography system as recited in claim 1, wherein the cassette ID is stored in a memory built in said electronic cassette.

14. The radiography system as recited in claim 1, wherein said first storage device is an internal storage device incorporated in said console, or an external storage device connectable to said console through a network.

15. The radiography system as recited in claim 1, wherein said first storage device is a memory built in said electronic cassette.

16. The radiography system as recited in claim 1, wherein said electronic cassette is of a wireless type that wirelessly communicates with said console.

17. The radiography system as recited in claim 1, wherein said housing of said electronic cassette is of a size according to ISO 4090:2001.

18. A console that communicates with an electronic cassette selected from among a plurality of electronic cassettes for radiography, said console comprising:
a correspondence data reading device for reading first correspondence data from a storage device, said first correspondence data indicating correspondence between a cassette ID of said electronic cassette and a label attached to a housing of said electronic cassette for making said electronic cassette visually distinguishable from other electronic cassettes, said cassette ID being used by said console for communication with the selected electronic cassette; and
a control device for displaying the label that corresponds to the cassette ID of the selected electronic cassette on a screen with reference to the first correspondence data, and
wherein said label includes a color as an element.

19. An electronic cassette comprising:
an image detector for detecting radiographic images when irradiated with radioactive rays;
a portable housing containing said image detector;
a labeling portion provided on said housing of said electronic cassette, a label for making said electronic cassette visually distinguishable from other electronic cassettes being attached to said labeling portion;
a communication device for communication with a console; and
a memory storing a cassette ID and first correspondence data, the cassette ID being used for communication with said console, the first correspondence data indicating correspondence between the label and the cassette ID, and
wherein said label includes a color as an element.

* * * * *